(12) United States Patent
Bhandari

(10) Patent No.: US 9,706,948 B2
(45) Date of Patent: Jul. 18, 2017

(54) INERTIAL SENSOR BASED SURGICAL NAVIGATION SYSTEM FOR KNEE REPLACEMENT SURGERY

(76) Inventor: Sachin Bhandari, Miami, FL (US)

(*) Notice: Subject to any disclaimer, the term of this patent is extended or adjusted under 35 U.S.C. 154(b) by 317 days.

(21) Appl. No.: 12/775,464

(22) Filed: May 6, 2010

(65) Prior Publication Data

US 2011/0275957 A1 Nov. 10, 2011

(51) Int. Cl.
*A61B 5/11* (2006.01)
*A61B 34/20* (2016.01)
*A61B 5/107* (2006.01)
*A61B 5/00* (2006.01)
*A61B 90/00* (2016.01)
*A61B 34/10* (2016.01)

(52) U.S. Cl.
CPC ............ *A61B 5/1114* (2013.01); *A61B 34/20* (2016.02); *A61B 5/107* (2013.01); *A61B 5/6828* (2013.01); *A61B 5/6829* (2013.01); *A61B 5/725* (2013.01); *A61B 2034/105* (2016.02); *A61B 2034/108* (2016.02); *A61B 2034/2048* (2016.02); *A61B 2090/3983* (2016.02); *A61B 2090/3991* (2016.02); *A61B 2505/05* (2013.01); *A61B 2562/0219* (2013.01)

(58) Field of Classification Search
CPC ........ A61B 19/5244; A61B 2019/5248; A61B 5/1071
USPC ........................................... 600/595; 606/102
See application file for complete search history.

(56) References Cited

U.S. PATENT DOCUMENTS

| | | | |
|---|---|---|---|
| 5,682,886 A | 11/1997 | Delp | |
| 5,871,018 A | 2/1999 | Delp | |
| 6,205,411 B1 | 3/2001 | DiGioia | |
| 6,551,325 B2 | 4/2003 | Neubauer | |
| 6,947,783 B2 | 9/2005 | Immerz | |
| 7,209,776 B2 | 4/2007 | Leitner | |
| 7,559,931 B2* | 7/2009 | Stone | 606/91 |
| 8,057,482 B2* | 11/2011 | Stone et al. | 606/102 |
| 2004/0243148 A1* | 12/2004 | Wasielewski | A61B 17/00 606/130 |
| 2005/0021044 A1* | 1/2005 | Stone et al. | 606/102 |

(Continued)

OTHER PUBLICATIONS

Yau et al, Intraobserver Errors in Obtaining Visually Selected Anatomic . . . , The Journal of Arthroplasty, Aug. 2005, pp. 591-601, vol. 20 No. 5, Elsevier, Amsterdam, DK.

(Continued)

*Primary Examiner* — Sean Dougherty
(74) *Attorney, Agent, or Firm* — Quarles & Brady LLP

(57) ABSTRACT

An inertial sensor based surgical navigation system for knee replacement surgery is disclosed. Inertial sensors composed of six-degree-of-freedom inertial chips, whose measurements are processed through a series of integration, quaternion, and kalman filter algorithms, are used to track the position and orientation of bones and surgical instruments. The system registers anatomically significant geometry, calculates joint centers and the mechanical axis of the knee, develops a visualization of the lower extremity that moves in real time, assists in the intra-operative planning of surgical cuts, determines the optimal cutting planes for cut guides and the optimal prosthesis position and orientation, and finally navigates the cut guides and the prosthesis to their optimal positions and orientations using a graphical user interface.

46 Claims, 20 Drawing Sheets

(56) References Cited

U.S. PATENT DOCUMENTS

| | | |
|---|---|---|
| 2005/0113659 A1* | 5/2005 | Pothier et al. ............... 600/372 |
| 2005/0197569 A1 | 9/2005 | McCombs |
| 2005/0234332 A1* | 10/2005 | Murphy ..................... 600/426 |
| 2005/0251026 A1* | 11/2005 | Stone ........................ 600/424 |
| 2006/0161051 A1* | 7/2006 | Terrill-Grisoni et al. .... 600/300 |
| 2006/0271056 A1* | 11/2006 | Terrill-Grisoni et al. ...... 606/84 |
| 2006/0271199 A1 | 11/2006 | Johnson |
| 2007/0032748 A1* | 2/2007 | McNeil ............... A61B 5/1038<br>600/595 |
| 2007/0123912 A1* | 5/2007 | Carson ........................ 606/130 |
| 2007/0270685 A1* | 11/2007 | Kang ........................... 600/424 |
| 2007/0287911 A1* | 12/2007 | Haid ...................... G01C 21/16<br>600/429 |
| 2008/0108912 A1* | 5/2008 | Node-Langlois ............ 600/587 |
| 2009/0000626 A1* | 1/2009 | Quaid ................ A61B 17/1764<br>128/898 |
| 2009/0204031 A1* | 8/2009 | McNames et al. .......... 600/595 |
| 2009/0247863 A1 | 10/2009 | Proulx |
| 2009/0318836 A1* | 12/2009 | Stone et al. ................. 600/595 |
| 2009/0318930 A1* | 12/2009 | Stone et al. ................. 606/102 |
| 2009/0318931 A1* | 12/2009 | Stone et al. ................. 606/102 |
| 2010/0016705 A1* | 1/2010 | Stone ........................... 600/407 |
| 2010/0063508 A1* | 3/2010 | Borja et al. .................. 606/88 |
| 2010/0064216 A1* | 3/2010 | Borja ................... A61B 17/154<br>715/705 |
| 2010/0100011 A1* | 4/2010 | Roche ................... A61B 5/103<br>600/587 |
| 2010/0204615 A1* | 8/2010 | Kyle ................... A63B 24/0006<br>600/595 |
| 2010/0250571 A1* | 9/2010 | Pierce ................. A61B 5/1076<br>707/758 |

OTHER PUBLICATIONS

Chauhan et al, Computer-Assisted knee arthroplasty . . . , Journal of Bone and Joint Surgery (British), Apr. 2004, pp. 372-377, vol. 86-B No. 3, Scty of B and J Srgry, Lndn, UK.

Stulberg et al, Computer-Assisted Total Knee Replacement Arthroplasty, Operative Techniques in Orthopaedics, Jan. 2000, pp. 25-39, vol. 10 No. 1, Elsevier, Amsterdam, DK.

Haaker et al, Computer-Assisted Navigation . . . , Clinical Orthopaedics and Related Research, Apr. 2005, pp. 152-159, No. 433, Lippincott Williams & Wilkins, Philadelphia, US.

* cited by examiner

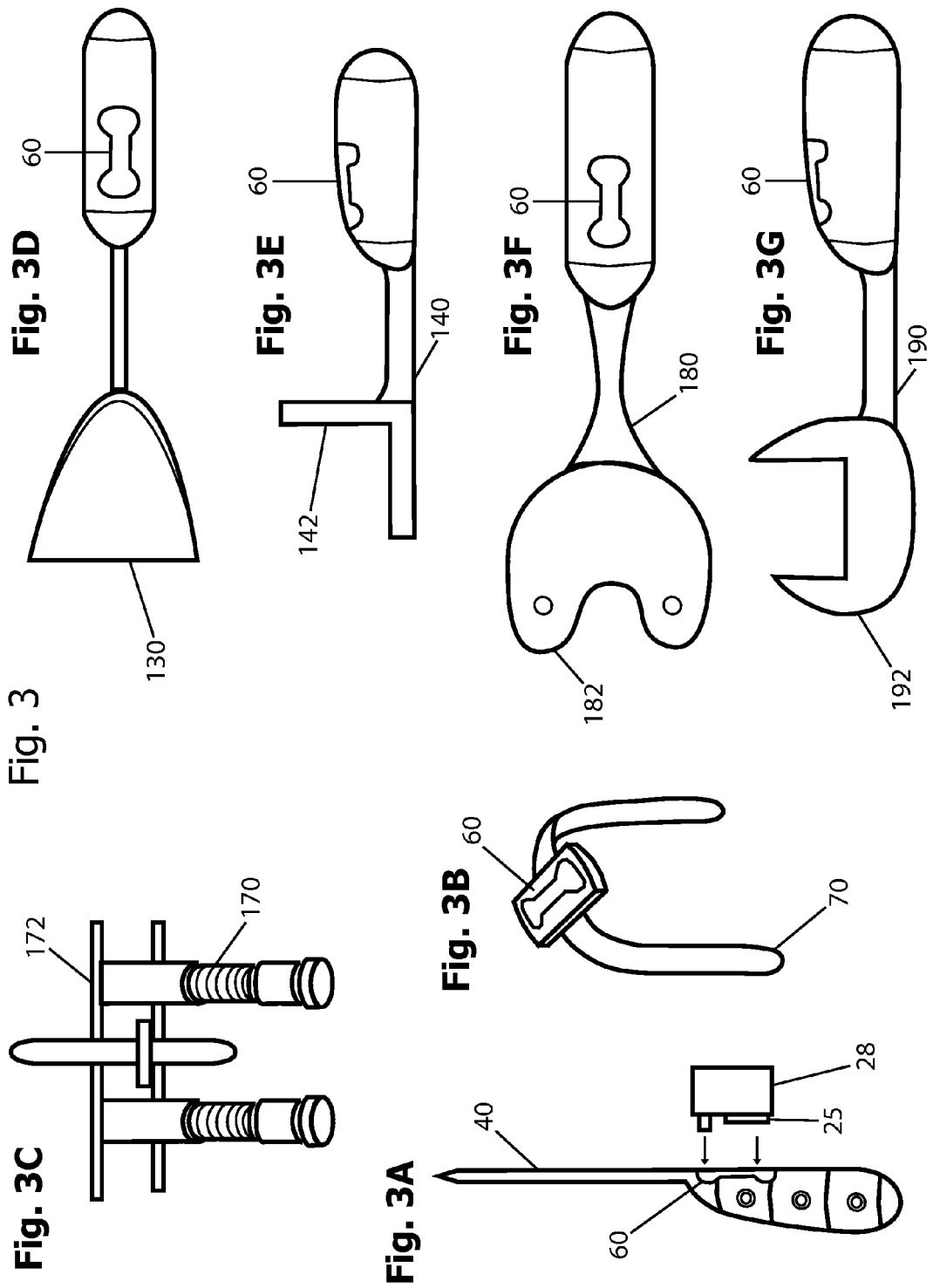

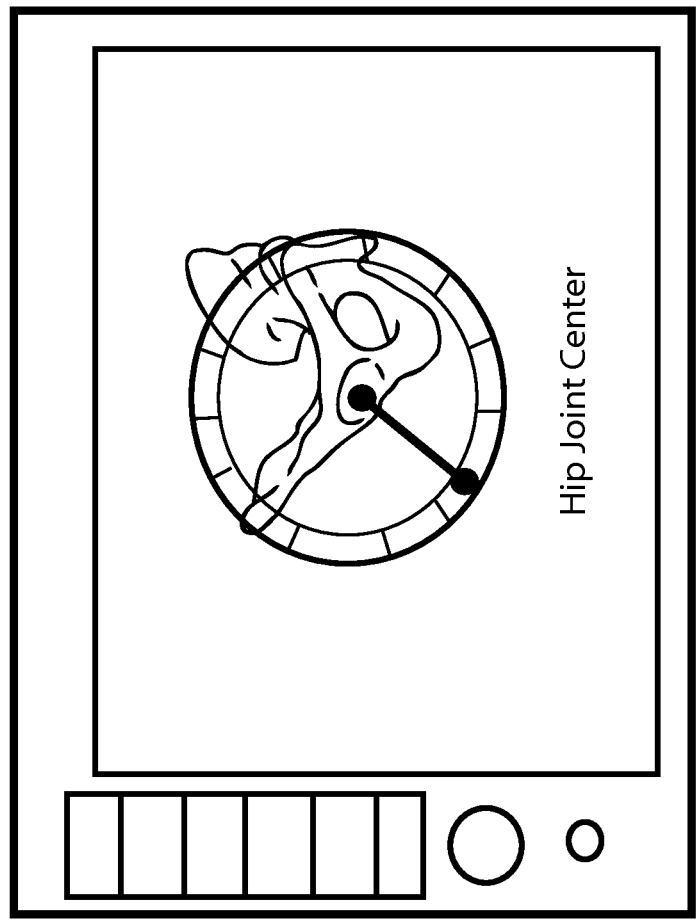
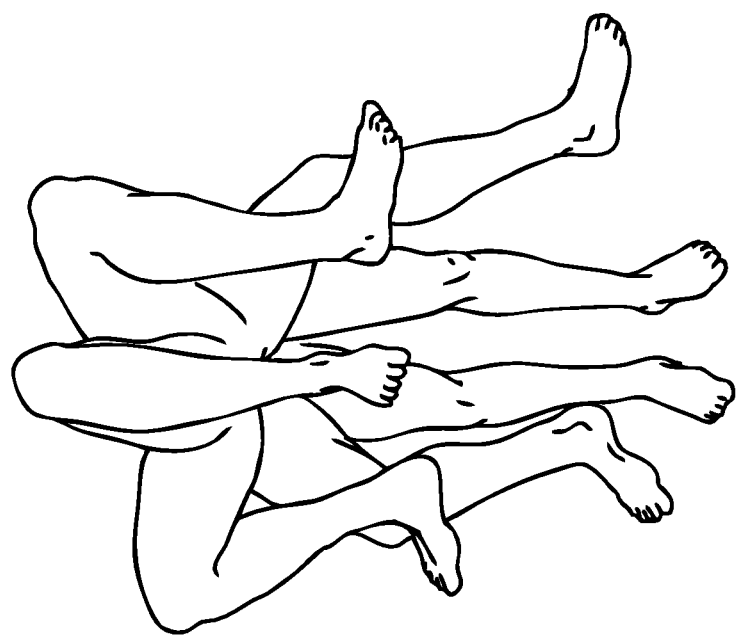
Fig. 8

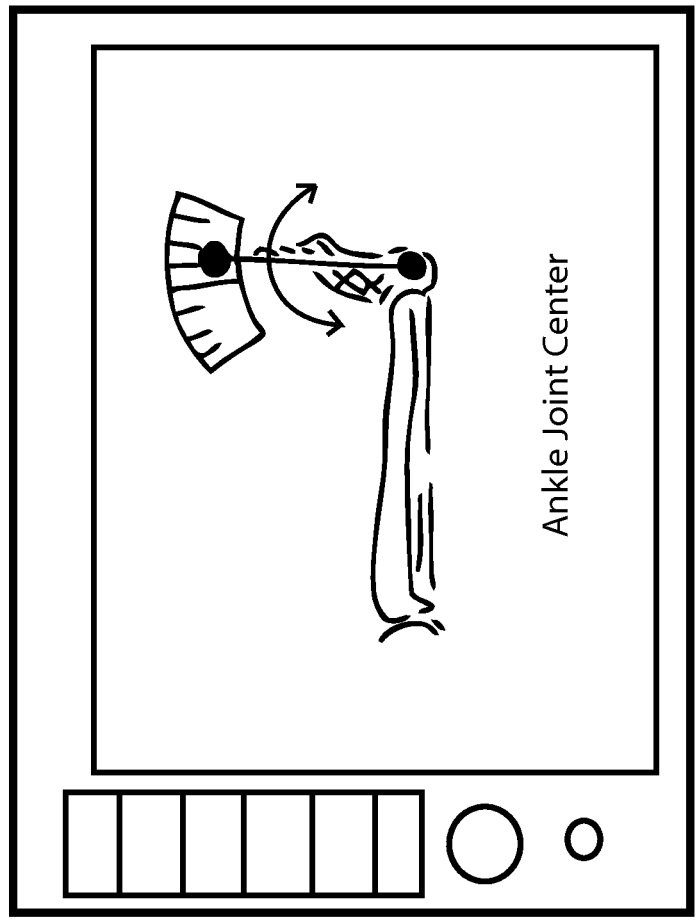
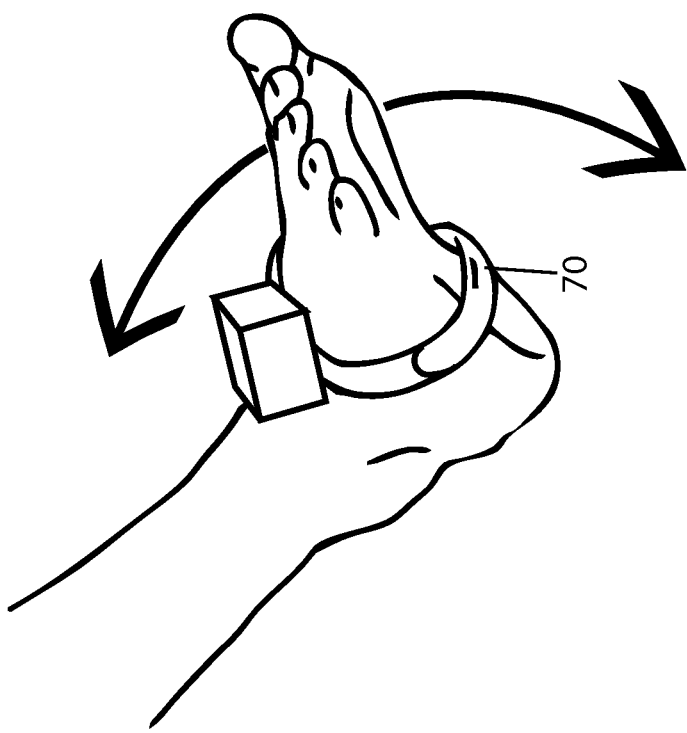
Fig. 9

Fig. 12
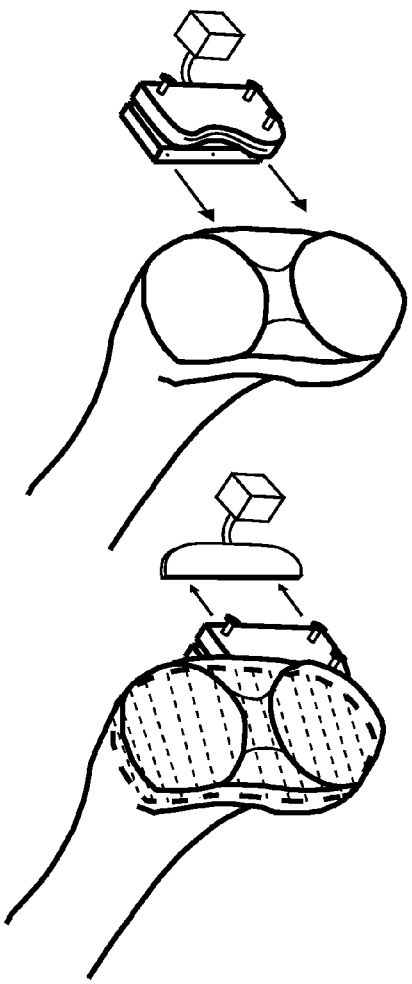
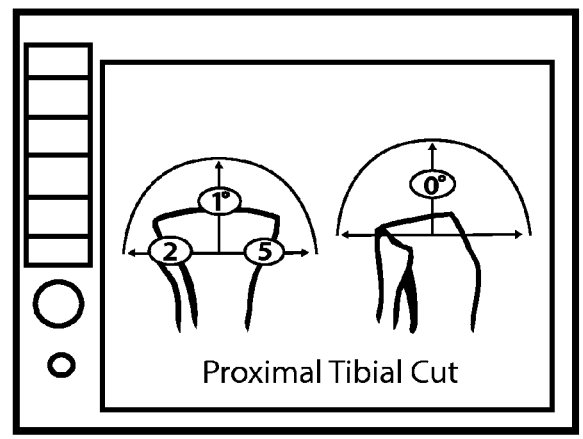
Proximal Tibial Cut
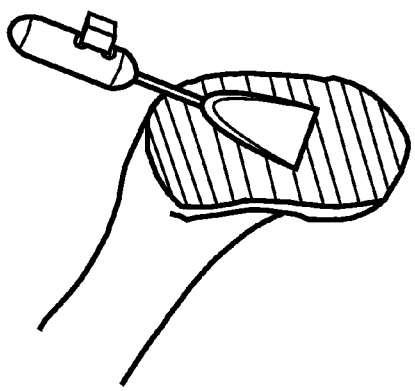
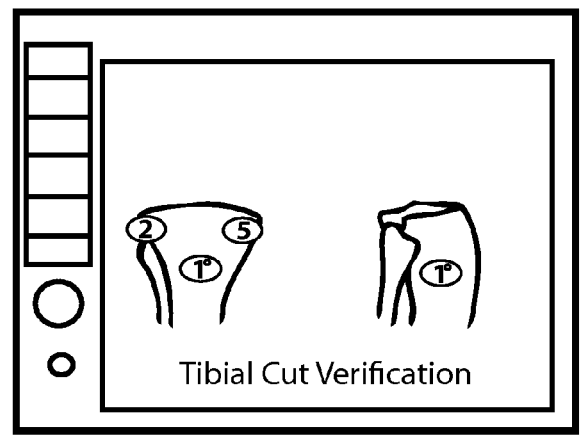
Tibial Cut Verification Fig. 13
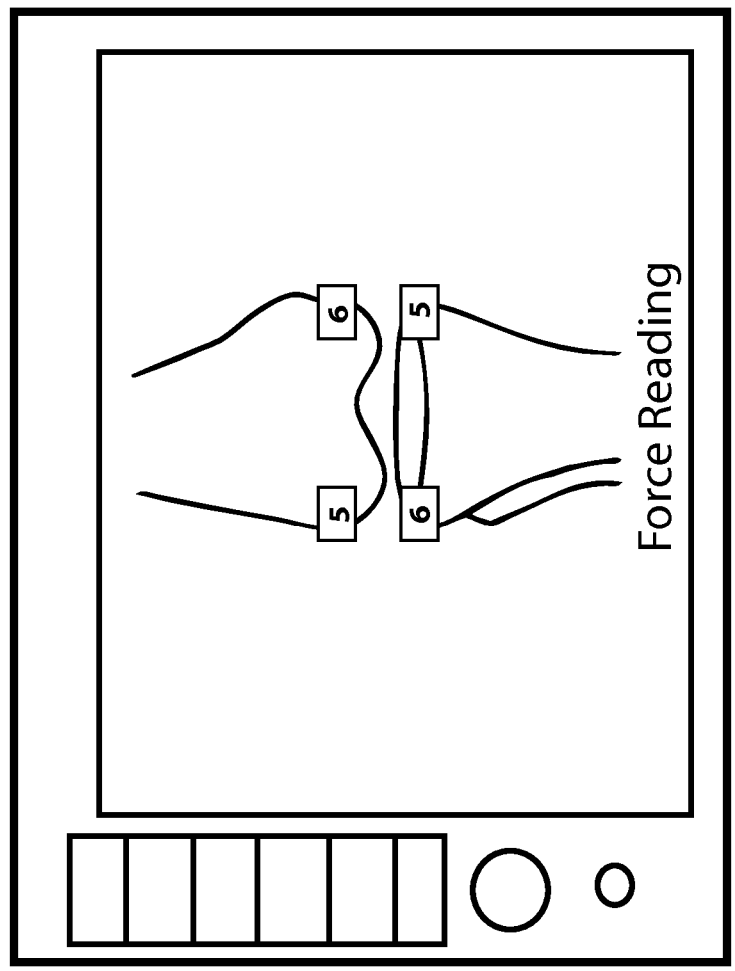
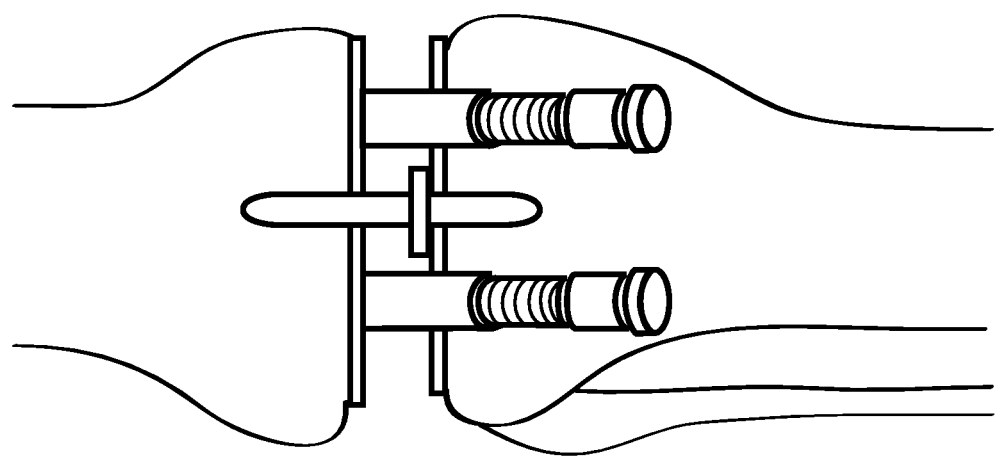

Fig. 16
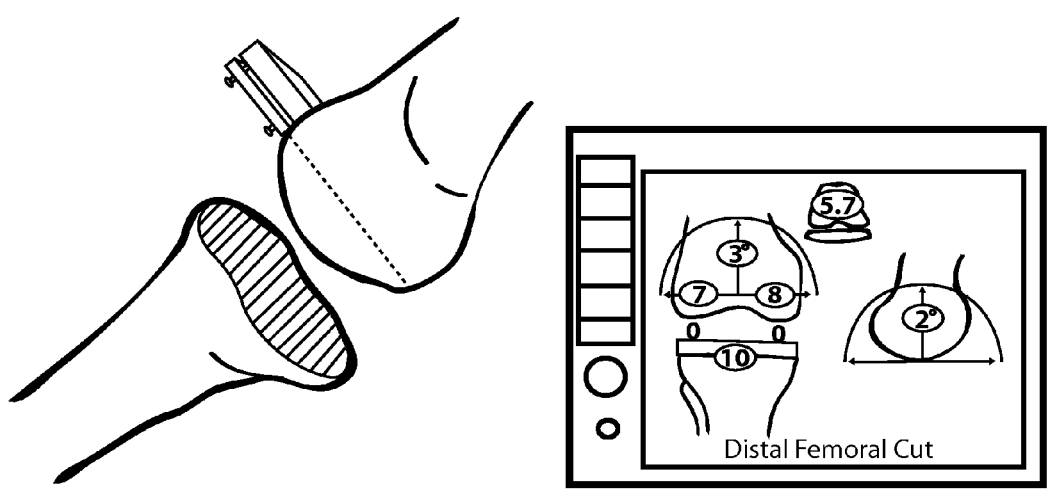
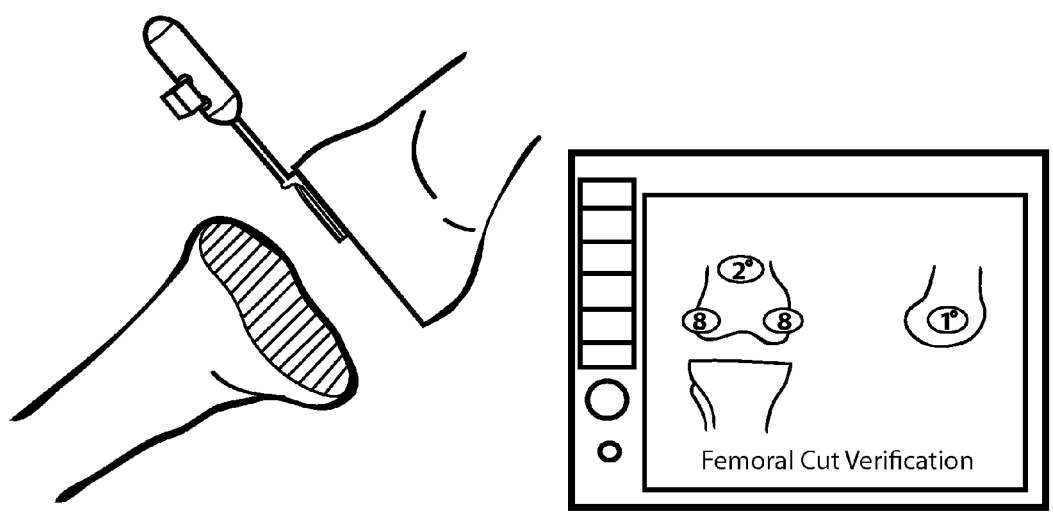

Fig. 17
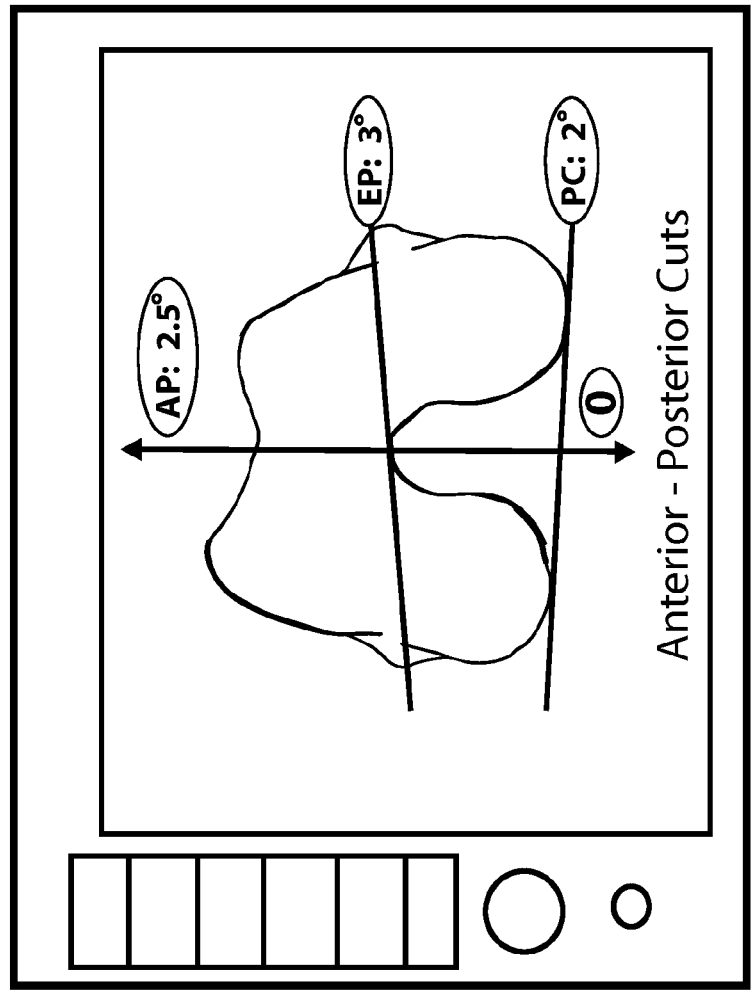
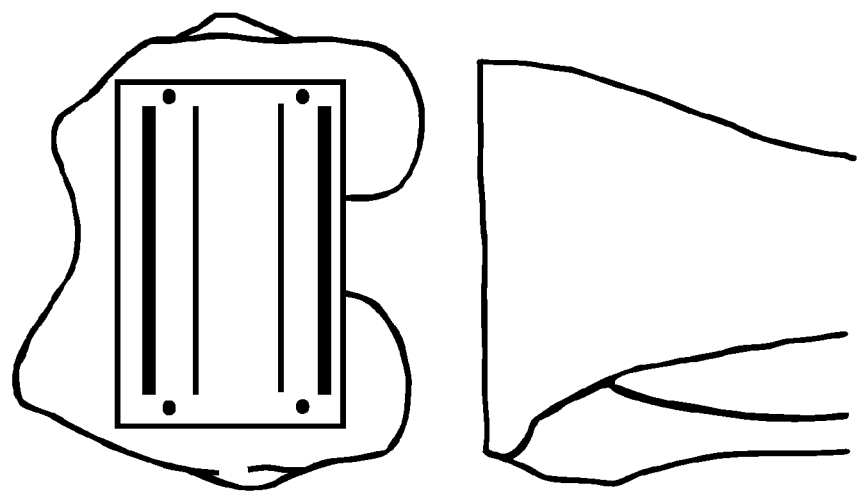

INERTIAL SENSOR BASED SURGICAL NAVIGATION SYSTEM FOR KNEE REPLACEMENT SURGERY

CROSS-REFERENCE TO RELATED APPLICATIONS

This application claims the benefit of provisional patent application Ser. No. 60/176,027 filed May 6$^{th}$, 2009.

FEDERALLY SPONSORED RESEARCH

Not Applicable

SEQUENCE LISTING OR PROGRAM

Not Applicable

BACKGROUND

Field of Invention

This invention relates to an inertial sensor based surgical navigation system for knee replacement surgery that maps various anatomical geometry, tracks the position and orientation of the lower extremity in real time, calculates optimal cutting planes and implant positions and orientations, assists the surgeon with cut planning, and provides navigation for surgical instruments and implants using a graphical user interface.

Prior Art

Modern knee replacement surgery was revolutionized in the late 1960s and the early 1970s by a series of improvements in prosthesis design. Particularly, the total condylar knee developed by Insall and others at the Hospital for Special Surgery set a standard for knee implants for many years to come. Unfortunately while knee replacement designs continued to improve in the intervening years, the actual procedure and surgical instrumentation for knee replacement surgery has remained for the most part quite similar to the original methods and tools used by Insall in the early 1970s.

In the conventional method of knee replacement surgery, still used by about 90% of practicing orthopaedic surgeons, the alignment of surgical cuts is implemented using complex mechanical instruments that are at times highly invasive. For example, the most common method of referencing the mechanical axis of the knee is to use an instrument known as the intramedullary rod. The intramedullary rod is specifically designed to align the femoral cut guides to the mechanical axis of the knee. Using the intramedullary rod involves drilling a pilot hole into the femur, reaming out the intramedullary canal, and placing a rod inside of the canal. The use of the rod in this manner drills out excess bone, damages the bone marrow of the femur, and has been shown to cause greater blood loss during surgery than using non-conventional instrumentation. Furthermore, the rod is not always accurate. The intramedullary rod aligns itself to the anatomic axis of the femur that runs along the intramedullary canal. The anatomic axis is known to be between 5 and 7 degrees offset from the mechanical axis of the knee. The exact amount of deviation for a particular patient is guesswork, and some patients may fall outside of the standard deviation for various reasons making their particular mechanical axis very difficult to ascertain using the rod. The intramedullary rod can also occasionally fracture inside of a patient's femur causing major complications during surgery.

Despite these problems, the intramedullary rod is a cornerstone of conventional surgical instrumentation used for knee replacement surgery.

Similarly, the extramedullary guide that is most commonly used to align the tibial cut guide in conventional surgery also has problems. The extramedullary guide is a large mechanical jig that runs parallel to the length of the tibia. Its purpose is to reference the anatomic axis of the tibia for the proximal tibial cut. Unlike the intramedullary rod however, the extramedullary guide remains on the outside of the bone. Although less invasive than its intramedullary counterpart, most designs of the guide suffer from a lack of adequate fixation. In other words, there is little actually holding the large mechanical jig in place other than the hands of one member of the surgical team. This is a problem because even a few millimeters of misalignment have been shown to have negative effects upon implant longevity. Using this type of free-floating guide and methodology, it is difficult to produce repeatable and accurate results when aligning the tibial cut guide for the proximal tibial cut.

In both situations, the mechanical jigs usually only allow for the alignment of the cut guides in the coronal plane, or from a front view of the knee. The alignment of the cut guides from the sagittal perspective, or from a side view, often has almost no means of verification other than the surgeon's eye.

Another problem with the conventional instrumentation and methodology is that most of the cut planning is done prior to the surgery, using standing x-rays. The problem with a standing x-ray is that if the stance of the patient is slightly rotated during the x-ray, meaning that if the patient's foot is not pointed straight ahead, the degree of varus/valgus deformity can be misjudged.

In short, the problems with conventional instrumentation is that the tools used for cut-planning and for aligning surgical cuts are only designed to work from the coronal perspective, and leave much room for human error producing results that are not always repeatable. Furthermore some of the instrumentation used, such as the intramedullary rod, is highly invasive.

By the late 1990s and the early 2000s the first surgical navigation systems came into being. The premise behind a surgical navigation system is that a sensor or group of sensors can align surgical cuts in a precise and accurate manner, while being less invasive than the conventional mechanical instrumentation of the past.

The surgical navigation systems for the most part use a camera and a set of optical trackers to track the position and orientation of the bones and surgical instruments during surgery. In most optical navigation systems, infra-red beams are shot from a camera to a set of reflective trackers, which then reflect the beams back to the camera. The reflection of the beams provides the computer system with information about the exact location of the trackers. In other optical navigation systems, a light emitting diode is fixed directly to the optical tracker, which then actively shoots infra-red beams to the camera. There are also numerous other forms of emitter/detector schemes that have been attempted, such as using ultra-sound in place of infra-red beams. In practice these navigation systems are virtually identical.

The trackers are used by the computer system to provide motion tracking information regarding the position and orientation of the bones and surgical instruments. A specialized point registration tool is used in these optical navigation systems, to map anatomically significant points on the bones into computer memory. The position and orientation of these points are saved, and their movement is tracked by the computer system. The registered points are used to generate a virtual model of the femur and tibia, and to calculate specific geometry of interest such as the joint centers of the hip, ankle, and knee, and the mechanical axis of the knee. This data is in turn used to calculate the optimal cutting planes to which the cut guides should be aligned for surgery. A graphical user interface on the computer screen is then able to instruct the surgeon exactly how to place the cut guide on the patient's knee without the use of the complex mechanical jigs of conventional surgery. This process is known as navigation. The navigation process has the advantage of aligning cut guides accurately and in a repeatable fashion, without being as invasive as conventional instrumentation. The computer is also able to provide the surgeon enough numerical and visual feedback, such that the cut guides can be aligned in both the coronal and sagittal planes, which the conventional instrumentation is also not capable of matching. Although the new computer based surgical instrumentation has solved many of the problems with the conventional instrumentation of the past, it also created some completely new ones.

The cameras in these systems typically have very specific constraints as to the angle and distance at which they must be located in relation to the operating table. In the Aesculap system for example, the camera has to be at a roughly 45 degree angle to the table, and must lie generally about two meters away from the knee. If the camera is placed outside of these constraints, it will not pick up the optical trackers. Furthermore, if the knee is moved such that the trackers are at an acute angle to the camera, the camera will have difficulty recognizing them. Also, the field of the camera is occasionally not wide enough to adequately capture all of the optical trackers from the hip to the ankle. This occurs when the trackers are not positioned on the bones well at the beginning of surgery. Finally, blood or tissue can also sometimes cover the reflective material or LEDs on the trackers, obstructing the camera's line-of-sight.

The trackers are purposefully designed to be large so that the camera can track them. A typical size envelope for a tracker is about 6 inches by 4 inches by 4 inches. As a result, they can quite easily be knocked off the bones inadvertently by a surgeon or nurse's elbow. The sheer size of the trackers can also make the angle of approach for other surgical instruments into the knee awkward and difficult to manipulate around.

In actual practice, line-of-sight between the camera and the optical trackers is a serious issue. In a typical surgery, there are multiple people hovering around the operating table that can physically obstruct the line-of-sight to the optical trackers. To avoid this from happening, one entire side of the operating table is off limits as to where the surgical team can stand. This is a real limitation that cannot be understated. Manipulating instruments carefully into a person's knee requires a fair amount of room, and two or three people crowded on the other side of the operating table creates an additional element of difficulty in the surgery.

In short, the optical navigation systems can align cut guides with greater precision and accuracy than conventional instrumentation. The optical navigation instrumentation is also far less invasive and simpler to use, because a graphical user interface on a computer screen renders the complex mechanical instrumentation of conventional surgery obsolete. The downside however is that line-of-sight issues as well as the large size of the optical trackers make surgery with an optical navigation system awkward and difficult at times.

Finally, in the mid 2000s a few inventors tinkered with the idea of using inertial sensors in surgery. Inertial sensors are sensors that are capable of detecting their own motion without the use of any external references. One reason why it may have taken so long for inertial sensors to trickle into the operating room is because previously the major applications for inertial sensors involved high speed vehicles. For example, inertial sensors are used to measure the acceleration of automobiles in order to deploy airbags, and the acceleration and angular velocity of jet planes for navigation purposes. Also the inertial sensors are generally not designed to take direct position and orientation measurements. A number of mathematical algorithms must first be applied to the raw data from the inertial sensors to derive the position and orientation information.

Haid (US 2007/0287911) describes the use of inertial sensors in surgery, and states how a series of quaternion algorithms and kalman filter algorithms might be used to derive accurate position and orientation coordinates from an inertial sensor. The Haid system does not describe how inertial sensors might be used to align surgical instrumentation or implants.

Wasielewski (US 2004/0243148) mentions attaching inertial sensors to various surgical tools and implants in knee replacement surgery. Unfortunately however, the invention Wasielewski describes does not calculate the optimal cutting planes from anatomically significant points, and thus does not actually navigate the cut guides using a graphical user interface. In fact, Wasielewski's system explicitly depicts the use of the intramedullary rod to reference the mechanical axis of the knee. Basically, Wasielewski describes a system which is comprised of a set of conventional instrumentation with inertial sensors attached. The drawback of Wasielewski's system is that it has all of the same flaws that the conventional instrumentation and methodology has. Furthermore, the system Wasielewski describes, mounts inertial sensors directly to anatomically significant points on the bones which is even more invasive than the conventional procedure.

Finally, Proulx (US 2009/0247863) also describes the use of inertial sensors to track the position and orientation of surgical instruments and implants. Proulx's invention, like Wasielewski's, does not calculate specific geometry like the mechanical axis of the knee from registered anatomical points, nor does it calculate the optimal cutting planes or component positions for surgical instrumentation. In other words, it also does not navigate cut guides or implants using a graphical user interface.

SUMMARY

The present embodiment of the invention is a surgical navigation system that makes use of inertial sensors to track bones and surgical instruments. The inertial sensors are individually comprised of two six-degree-of-freedom inertial chips whose measurements are processed through a series of integration, quaternion, and kalman filter algorithms. The processed data from the inertial sensors yields the X, Y, Z position and Yaw, Pitch, Roll orientation of the elements being tracked by the inertial sensors. The inertial sensors are incorporated into a specialized set of surgical instrumentation which is used in conjunction with the computer system to: register anatomically significant points, calculate joint centers and the mechanical axis of the knee, develop a visualization of the lower extremity that moves in real time, determine the optimal cutting planes for the surgical cuts, assist the surgeon in intra-operative cut planning, determine the optimal prosthesis position and orientation, and finally navigate the cut guides and the prosthesis to their optimal positions and orientations using a graphical user interface.

Like the optical navigation system, the inertial navigation system aligns the cut guides and implants three-dimensionally, as opposed to only from the coronal perspective. Furthermore, the inertial navigation system aligns the cut guides without the use of complex mechanical jigs, such as the intramedullary rod. Thus compared to conventional instrumentation, the inertial navigation system aligns cut guides and implants with greater accuracy and precision, while still being less invasive.

Compared to the optical navigation systems, the inertial navigation system can perform the entire knee replacement operation reaping the benefits of computer assisted navigation without any of the line-of-sight issues that plague all emitter/detector schemes. The inertial navigation system is able to do this, because it is based off of a fundamentally different technology that does not need an external reference to track its own motion. The inertial navigation system frees up operating space, by allowing the surgical team to use both sides of the operating table, and by allowing other surgical instruments improved access into the joint. Furthermore, the sensor technology of the inertial navigation system costs significantly less than the average optical navigation system. Finally some aspects of the computer assisted navigation process have been improved upon in the inertial navigation system described herein.

Other embodiments of the invention differ slightly from the present embodiment described above.

DRAWINGS

Figures

FIG. 3 shows various surgical instruments used in surgery.

FIG. 8 shows the rotation of the lower extremity used to determine the center of the hip, and the accompanying screenshot from the graphical user interface.

FIG. 9 shows the rotation of the foot used in part to determine the center of the ankle, and the accompanying screenshot from the graphical user interface.

FIG. 12 shows the tibial cut guide being navigated to its optimal cutting plane, the tibial insertion piece and inertial sensor being removed from the cut guide, the cut check tool verifying the accuracy of the cut, and the accompanying screenshots from the graphical user interface.

FIG. 13 shows the ligament balancer inserted into the knee, and the accompanying screenshot from the graphical user interface.

FIG. 16 shows the distal femoral cut guide being navigated to its optimal cutting plane and the accompanying screenshots from the graphical user interface.

FIG. 17 shows the AP cut guide being navigated to its optimal cutting planes and the accompanying screenshot from the graphical user interface.

Figure 1:
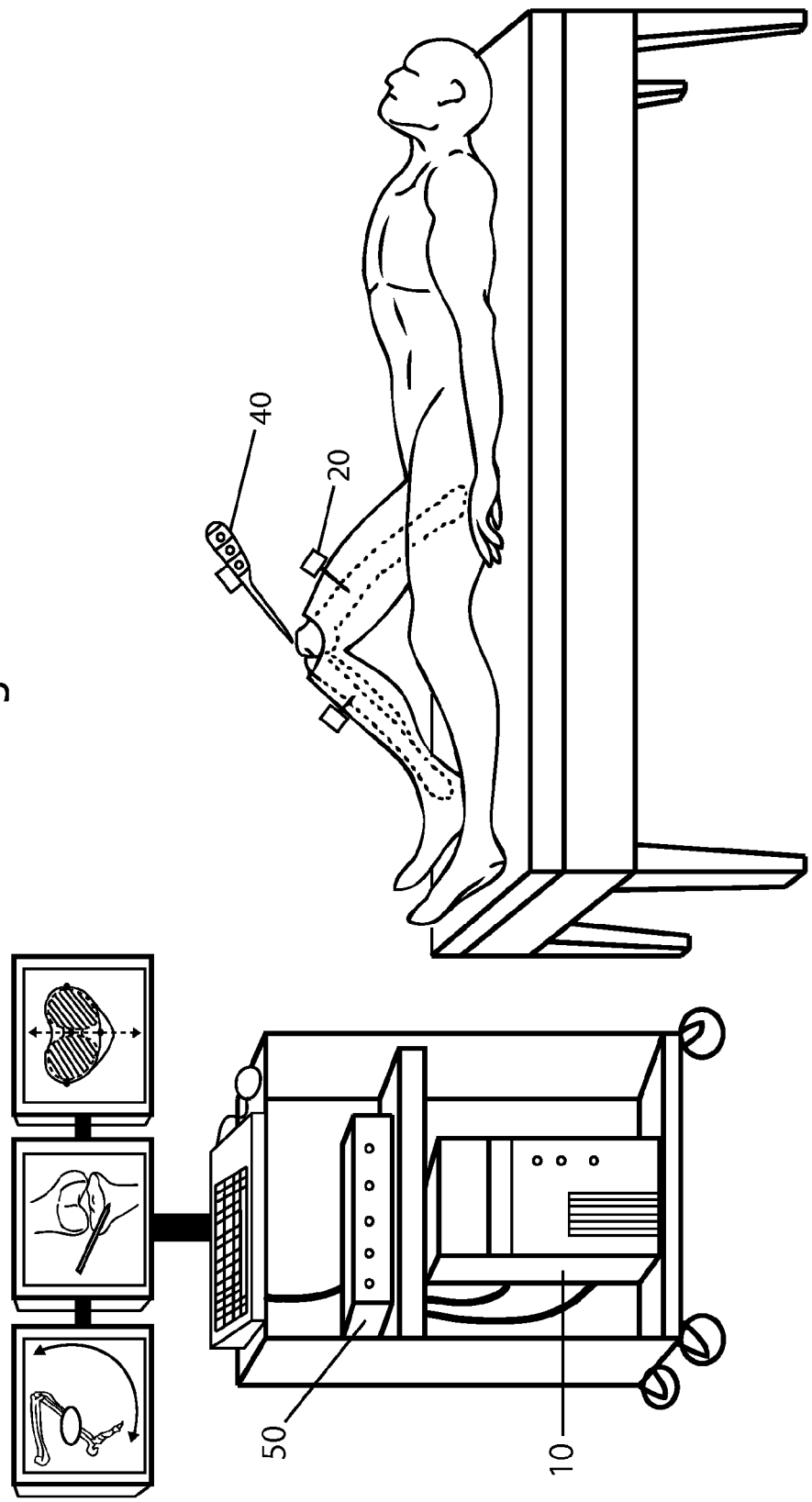
FIG. 1 shows an image of the surgical navigation system as anatomical landmarks are being mapped.

REFERENCE NUMERALS 10 computer system
20 tibiofemoral inertial sensor
21 cortical pin
22 cortical pin flange
23 bone screw
24 bone grip fixation tool
25 universal housing flange
26 bone grip fixation flange
27 stop on universal housing flange
28 instrument inertial sensor
30 calibration box
40 pointer device
50 inertial sensor hub
60 universal docking bay
70 foot strap
80 tibial cut guide
81 tibial cut guide pin holes
82 tibial cutting slot
84 base of the tibial cut guide
86 tibial fine adjustment screws
90 tibial insertion piece
92 AP cut guide
94 anterior cutting slot
96 AP insertion piece
100 inertial sensor docking bay
110 cut guide flange
120 cut guide inertial sensor
130 cut check tool
140 femoral sizing tool
142 L-shaped head on femoral sizing tool
150 distal femoral cut guide
151 distal femoral pin holes
154 base of the distal femoral cut guide
152 distal femoral cutting slot
156 femoral fine adjustment screws
160 distal femoral insertion piece
170 ligament balancer
172 force transducers on ligament balancer
180 tibial component implant tool
190 femoral component implant tool
182 tibial trial component 192 femoral trial component

DETAILED DESCRIPTION

Surgical Hardware

FIG. 1 shows some of the surgical hardware of the inertial sensor based surgical navigation system. The computer system 10 is comprised of three monitors, a keyboard, a mouse, and a standard upright workstation. In an alternate embodiment of the invention, a set of touch-screen monitors is used in place of the standard monitors. Also a handheld device with a visual display such as a smartphone is used in conjunction with the monitors in alternate embodiments of the invention. The handheld device is used to interact with the computer system directly from the surgeon's hand. The purpose of the computer system is to perform calculations and to provide a user interface for the surgeon to interact with.

FIG. 1 also shows an inertial sensor hub 50 that is connected to the computer system via a USB port. The inertial sensor hub is used for wireless communications with the inertial sensors and may also be used for additional computations so as to relieve the computer system's processing power.

In FIG. 1, tibiofemoral inertial sensors 20 are shown pinned directly to the femur and tibia. The tibiofemoral inertial sensors 20 can be fixed either inside or outside of the incision used for surgery. The tibiofemoral inertial sensors are used to track the position and orientation of the two bones.

A pointer device 40 shown in FIG. 1 is used to register anatomical landmarks, surfaces of the bones, and important anatomical axes along the surfaces of the bones. The mapping process implemented by the pointer device is used to track the position and orientation of anatomically significant points, surfaces, and axes of the two bones.

FIG. 2 takes a closer look at the housings for the inertial sensors and how they interact with the other surgical equipment. The inertial sensors fall into three different categories with unique housings for each distinct category. Tibiofemoral inertial sensors 20, shown in FIG. 2A, are used to track the position and orientation of the femur and tibia. Instrument inertial sensors 28, shown in FIG. 2B, are used to track the position and orientation of the surgical instruments excluding the cut guides. Cut guide inertial sensors 120, shown in FIGS. 2C to 2E, are used to track the position and orientation of the cut guides.

All three types of the inertial sensors are designed to be detachable from the tools that they interact with. This allows for the easy replacement of the sensors in case of malfunction during surgery. Also, many of the tools that the sensors interact with are used only intermittently throughout the surgery. By making the inertial sensors interchangeable among the surgical tools, a limited number of inertial sensors can be cycled through the tools as they are being used and thus reduce the overall cost of the system. The cost of technology is an important advantage of the inertial navigation system over optical navigation systems. The total cost of all of the sensors for one complete inertial navigation system is roughly $6000 at the present time. By comparison the camera alone in an optical navigation system can cost more than $10,000. Also, the size envelope of an individual inertial sensor is about 2 cubic inches. For an optical tracker, depending upon the particular system, the size envelope is about 6 inches by 4 inches by 4 inches. The smaller footprint of an inertial sensor is a significant advantage over the optical trackers, because it frees up space near the incision for a surgeon to handle tools. Space in and around the incision is quite limited, and the large optical trackers often permit the tools to enter the joint only at awkward angles of approach. The problem is exacerbated because the optical trackers must always maintain line-of-sight with a camera for an optical navigation system to work. In effect this means that one entire side of the operating table is unavailable as standing room for the surgical team, or else a member of the team might block the camera's view of an optical tracker. The surgical team, composed of usually about two or three people, is then forced to hover over the other side of the operating table with each member working in a limited space, and their elbows constantly at risk of knocking over the large optical trackers. Also, the surgical team must take care that stray blood and tissue does not obscure the optical tracker's line-of-sight with the camera. The inertial sensors by contrast entirely eliminate line-of-sight as an issue, by tracking the position and orientation of the bones and instruments without the use of an external reference such as a camera. Space on both sides of the operating table can be fully utilized, and the surgeon can handle the tools more akin to a conventional surgery while still deriving the benefits of using a navigation system.

Figure 2A:
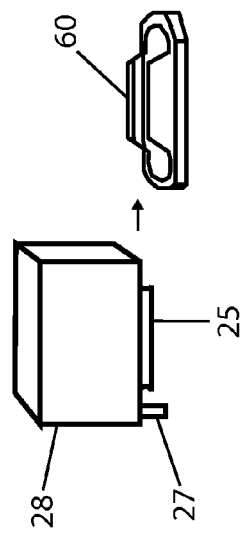
FIG. 2 shows the housings of the inertial sensors, attachments to the housings, and the cut guides used in surgery.

In FIG. 2A, a tibiofemoral inertial sensor 20 can be seen with two alternate housings for different embodiments of the invention. In one configuration, cortical pins 21 are used to secure the tibiofemoral inertial sensor 20 to the bone by means of a cortical pin flange 22. In a second configuration, the tibiofemoral inertial sensor 20 is secured with a single bone screw 23 used in concert with a bone grip fixation tool 24. The bone grip fixation tool 24 attaches securely to a bone grip fixation flange 26 located on the inertial sensor's housing.

Figure 2B:
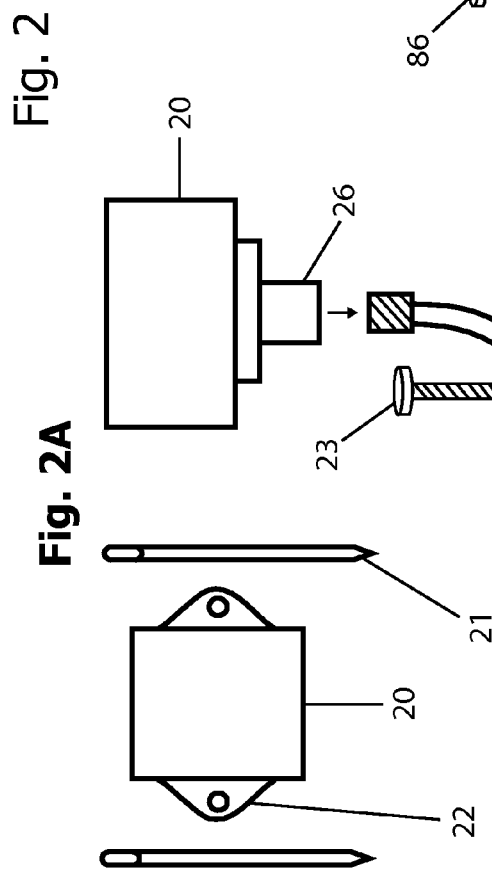

In FIG. 2B, an instrument inertial sensor 28 has its own specialized housing that allows it to attach universally to other surgical instruments. A universal housing flange 25 on the sensor slides into a universal docking bay 60. The universal docking bay 60 is shown by itself, though in reality it is incorporated directly into the housing of the other surgical instruments. The universal housing flange 25 has a stop 27 that limits its motion. The sensor is held securely in place by close geometric tolerances between the flange and the docking bay. The purpose of the universal docking bay 60 is to allow instrument inertial sensors 28 to be interchangeable among different surgical tools.

Figure 2C:
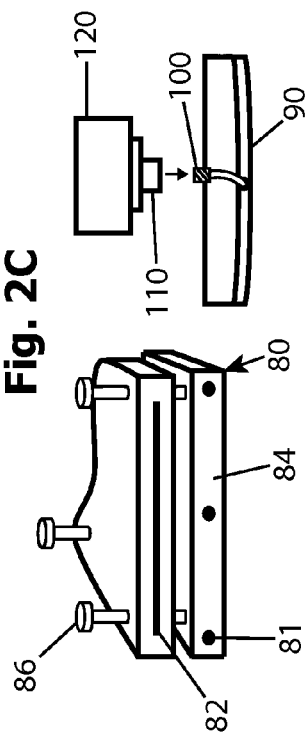

In FIG. 2C, a tibial cut guide 80 is shown with a base 84 that is pinned directly to the tibia by means of several pinholes 81. The cutting slot 82 of the tibial cut guide 80 is suspended above the base 84 by three screws 86. In surgery, once the base 84 has been pinned to the tibia, the screws 86 allow for the further adjustment of the distal/proximal position, coronal angle, and sagittal angle of the cutting slot 82, by altering the plane along which the cutting slot 82 interacts with the bone. A tibial insertion piece 90 is placed into the cutting slot 82 of the tibial cut guide 80, and held in place by close geometric tolerances. The other end of the tibial insertion piece 90 has an inertial sensor docking bay 100 that allows a cut guide inertial sensor 120 to mount by means of a cut guide flange 110. The purpose of the tibial insertion piece 90 is to provide a means by which the cut guide inertial sensor 120 can track the position and orientation of the cutting slot 82 on the tibial cut guide 80, and thus the true cutting plane.

Figure 2D:
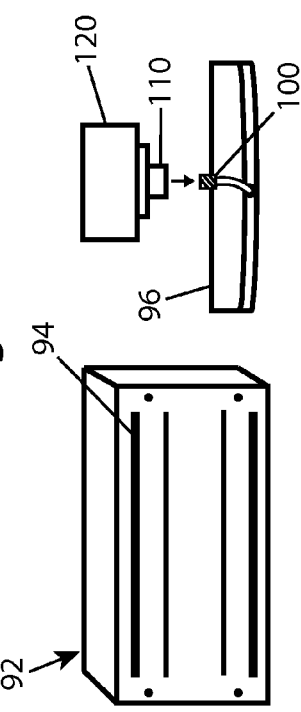
Figure 2E:
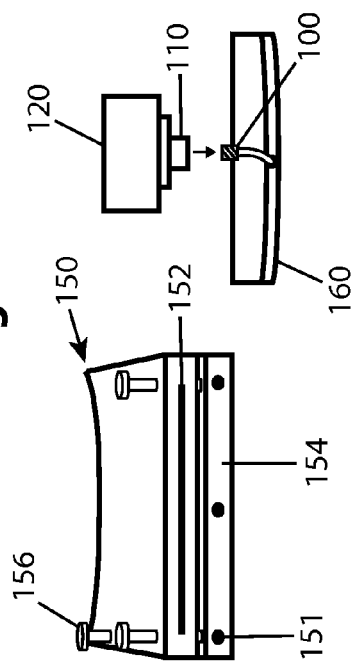

Similarly, in FIG. 2E a distal femoral cut guide 150 is shown with a base 154 that is pinned directly to the femur via pinholes 151. Screws 156 suspend the distal femoral cutting slot 152 above the base 154 and allow for the fine adjustment of the cutting plane after the base 154 has been pinned to the bone. A distal femoral insertion piece 160 slides into the distal femoral cutting slot 152. The distal femoral insertion piece 160 allows a cut guide inertial sensor 120 to attach by means of an inertial sensor docking bay 100, which secures to a cut guide flange 110 on the inertial sensor's housing. In this manner, the distal femoral insertion piece 160 allows the cut guide sensor 120 to track the position and orientation of the distal femoral cutting slot 152.

In FIG. 2D, an AP cut guide 92 is shown with an AP insertion piece 96 that slides into the anterior cutting slot 94. Similarly, the cut guide inertial sensor 120 has a cut guide flange 110 that mounts to the inertial sensor docking bay 100 allowing the position and orientation of the AP cut guide 92 to be tracked. The AP cut guide does not have any fine adjustment screws.

FIG. 3 depicts the surgical instruments that are used in conjunction with the instrument inertial sensors. FIG. 3A depicts a pointer device 40 that is used to register anatomical landmarks and surfaces along the bones. The pointer device 40 has a universal docking bay 60 to which an instrument inertial sensor 28 is attached by means of the universal housing flange 25. In this particular embodiment of the invention, the pointer device is designed with a large grip that has several push buttons embedded in the housing for data entry. In an alternate embodiment of the invention, the pointer device is devoid of push buttons and instead uses a foot pedal for data entry. In another alternate embodiment of the invention, the pointer device is devoid of push buttons and is configured to recognize specific gestures, such as an abrupt twist along one axis, to constitute data entry.

In FIG. 3B, a foot strap 70 is illustrated, which is used to securely fasten an inertial sensor to the foot during surgery. The foot strap 70 aids in the determination of the center of the ankle joint. A universal docking bay 60 allows for an instrument inertial sensor to track the position and orientation of the foot during surgery.

In FIG. 3C, a ligament balancer 170 is present. The ligament balancer is inserted in between the femur and tibia to measure the ligament tension in the medial and lateral compartments of the knee during surgery. The ligament balancer has force transducers 172 on its surfaces that interact with the bone. The ligament balancer is not tracked by an inertial sensor.

FIG. 3D illustrates a cut check tool 130, which is used for checking the accuracy of the cutting plane along the exposed bone surface after a surgical cut is made. The cut check tool 130 has a universal docking bay 60, allowing an instrument inertial sensor to track its position and orientation.

In FIG. 3E, a femoral sizing tool 140 is used to measure the size of the femur and determine the optimal size of the femoral component. The femoral sizing tool 140 has an L-shaped head 142 that is used to make solid contact with the posterior and distal aspect of the femoral condyles. The femoral sizing tool 140 also has a universal docking bay 60 to which an instrument inertial sensor can attach. The femoral sizing tool references the posterior aspect of the femur when determining the femoral component size. In an alternate embodiment of the invention, the femoral sizing tool references the anterior aspect of the femur instead.

FIG. 3F and FIG. 3G show a tibial implant tool 180 and a femoral implant tool 190. A trial tibial component 182 and a trial femoral component 192 are shown attached to their respective tools. Both tools have a universal docking bay 60, that allow them to be navigated by instrument inertial sensors. The tools are used to position and implant the tibial and femoral components during surgery.

Figure 4:
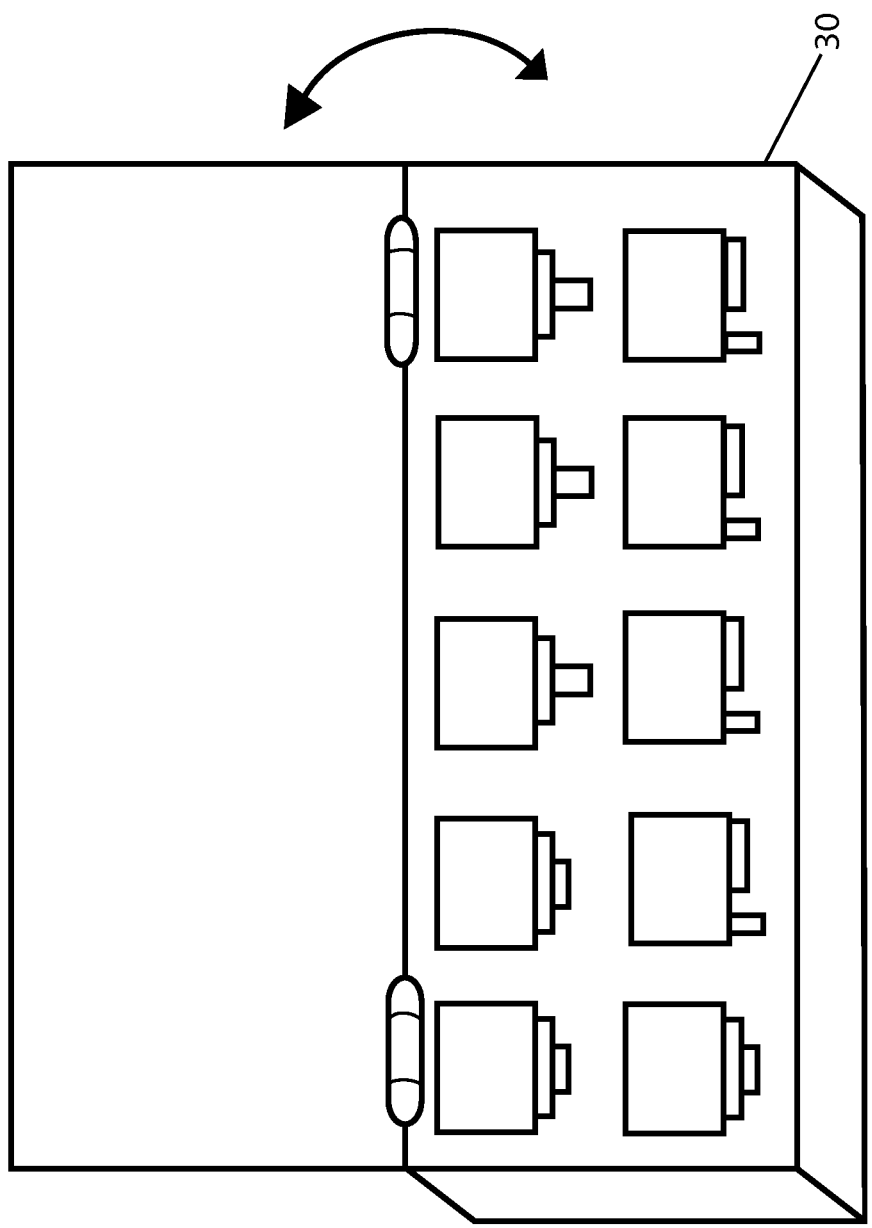
FIG. 4 shows the calibration box that is used to hold the inertial sensors during the calibration procedure.

FIG. 4 illustrates a calibration box 30. The calibration box 30 is used to hold the inertial sensors during the calibration procedure. The box is carefully machined such that the sensors are held at precisely known distances apart. This allows the sensors to be plotted in the computer system on a common coordinate system. The calibration box 30 depicts ten inertial sensors. Two tibiofemoral sensors are pinned at all times to the tibia and femur. One instrument inertial sensor is used continuously on the pointer device. Two cut guide inertial sensors are cycled through the cut guides over the course of the procedure. Two instrument inertial sensors are cycled through the remaining surgical instruments. Finally one spare sensor of each category is present in the calibration box as well, to be used only in the event of a sensor malfunction. In alternate embodiments of the invention, the number of inertial sensors used may vary. The use of the calibration box is explained in greater detail in the operation and software sections.

Hardware Circuitry

Figure 5:
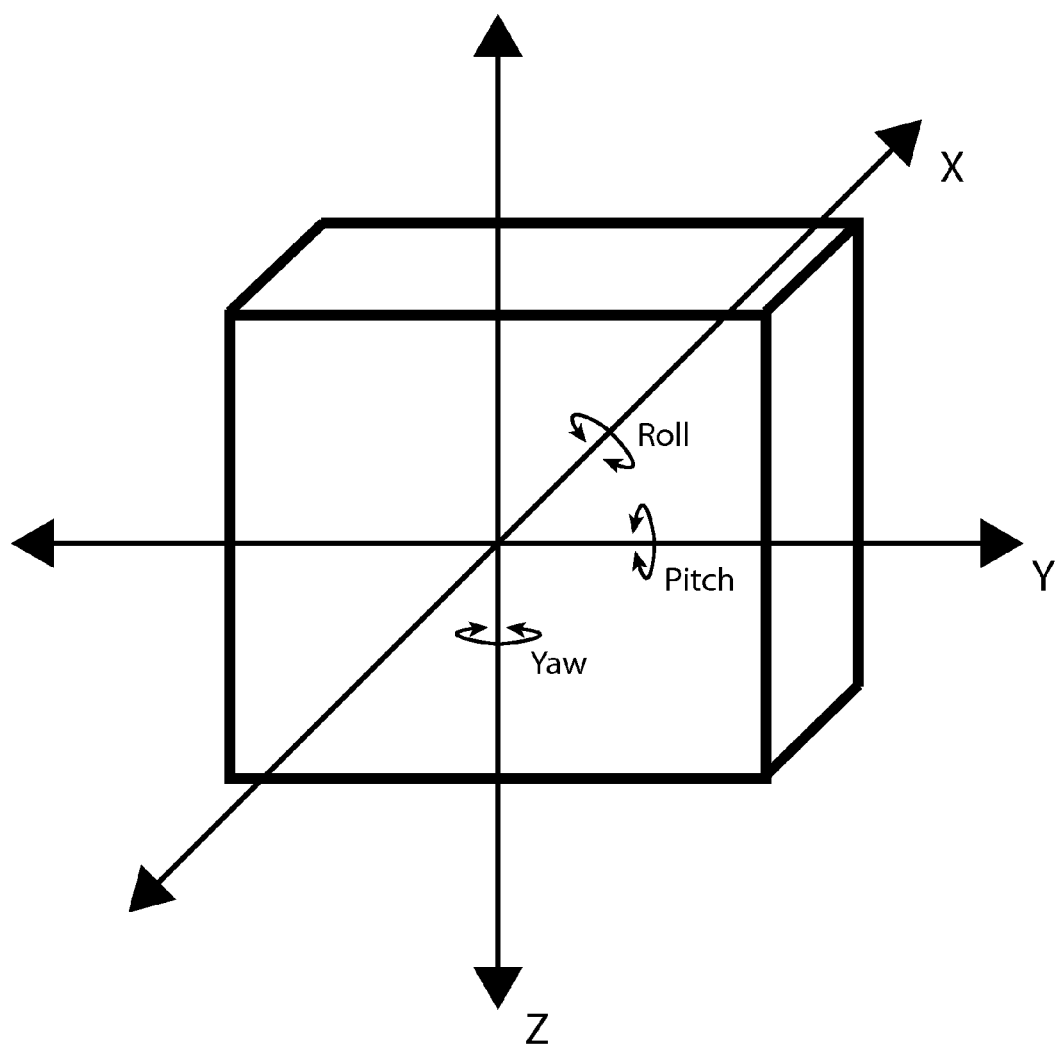
FIG. 5 shows the X, Y, Z position axes and the Yaw, Pitch, Roll orientation axes with respect to an inertial sensor.

This particular embodiment of the invention uses a six-degree-of-freedom inertial chip known as the ADIS16354 to construct the inertial sensor. The ADIS16354 is manufactured and sold by Analog Devices. The inertial chip is able to measure acceleration along its X, Y, and Z-axis as well as measure its Yaw, Pitch, and Roll angular velocity. This raw data is used to calculate the X, Y, Z position and Yaw, Pitch, Roll orientation of the inertial chip as depicted in FIG. 5.

The ADIS16354 has built-in temperature compensation, which is an important feature because temperature fluctuations are a significant source of drift in other inertial chips. The ADIS16354 also has specialized functions on board that allow its acceleration and angular velocity measurements to be zeroed when stationary. These functions aid greatly in the initial calibration of the chip. Finally, the ADIS16354 has a status register that is able to detect if its internal circuitry is malfunctioning. This status register is used in the present embodiment of the invention to notify a surgeon when to swap out malfunctioning inertial sensors.

Any inertial chip, or combination of inertial chips, whose X, Y, Z position and Yaw, Pitch, Roll orientation can be calculated without the use of an external reference, such as a laser or camera, could be used to construct the complete inertial sensor in other various embodiments of the invention. For example, a three axis accelerometer that measures acceleration along its X, Y, and Z axis could be paired with a three axis gyroscope that measures its Yaw, Pitch and Roll angular velocity to construct a complete six-degree-of-freedom inertial sensor.

The inertial chips are variously known as accelerometers, gyroscopes, orientation sensors, tilt sensors, inertial measurement units, and inertial navigation units. Also, the inertial chips are occasionally integrated with magnetometers, or sensors that can measure their orientation with respect to the Earth's magnetic axes. The inertial chip/magnetometer combinations are also known as attitude heading reference systems and could be used in other embodiments of the invention as well.

To derive the position and orientation from the raw data of the ADIS16354, the data is processed through a series of integration, quaternion, and kalman filter algorithms. The X, Y, Z acceleration data is integrated twice to calculate the X, Y, Z position of the inertial chip. The angular velocity data can be processed using a quaternion algorithm or alternatively a specialized integration algorithm taking into account the effect of simultaneous rotations. From either of these two algorithms, the Yaw, Pitch, Roll orientation of the inertial chip can be determined. Finally all of the data is run through a kalman filter algorithm. The kalman filter algorithm is used to root out error accumulation, and increase the precision of the position and orientation calculations.

The kalman filter algorithm is necessary because any slight bias or error in the acceleration or angular velocity measurements can lead to a rapid accumulation of error. This occurs because small errors in the measurement of acceleration and angular velocity are integrated into progressively larger errors in the calculation of position and orientation. The running position and orientation coordinates are calculated from the previous position and orientation coordinates that may already be inaccurate. Thus error in the position and orientation calculations is cumulative. Furthermore, hundreds of measurements are taken per second by the inertial chip so without some form of a kalman filter algorithm, the position and orientation coordinates would be wildly inaccurate within a few minutes.

For the kalman filter algorithm to effectively root out error, it is optimal to take measurements from at least two six-degree-of-freedom inertial chips per each complete inertial sensor. The two or more inertial chips are physically arranged on the sensor such that their sensitive axes are parallel to one another. The additional six-degree-of-freedom inertial chips take redundant measurements of the X, Y, and Z acceleration and the Yaw, Pitch, and Roll angular velocity. The multiple acceleration and angular velocity measurements obtained in parallel from the inertial chips serve as the input signals for the kalman filter. Aided by the supporting information from the additional inertial chips, the kalman filter algorithm provides an estimated value for the deviation, or error, of the X, Y, Z position coordinates and the Yaw, Pitch, Roll orientation coordinates for the complete inertial sensor. The filter operates recursively with the previous measurements and their corrections being filtered again with each new set of measurements taken from the inertial chips. In the alternate embodiment of the invention in which magnetometers are incorporated into the individual inertial chips, the Yaw, Pitch, Roll angular velocity measurements from the magnetometers are used as additional input to the kalman filter.

Figure 6:
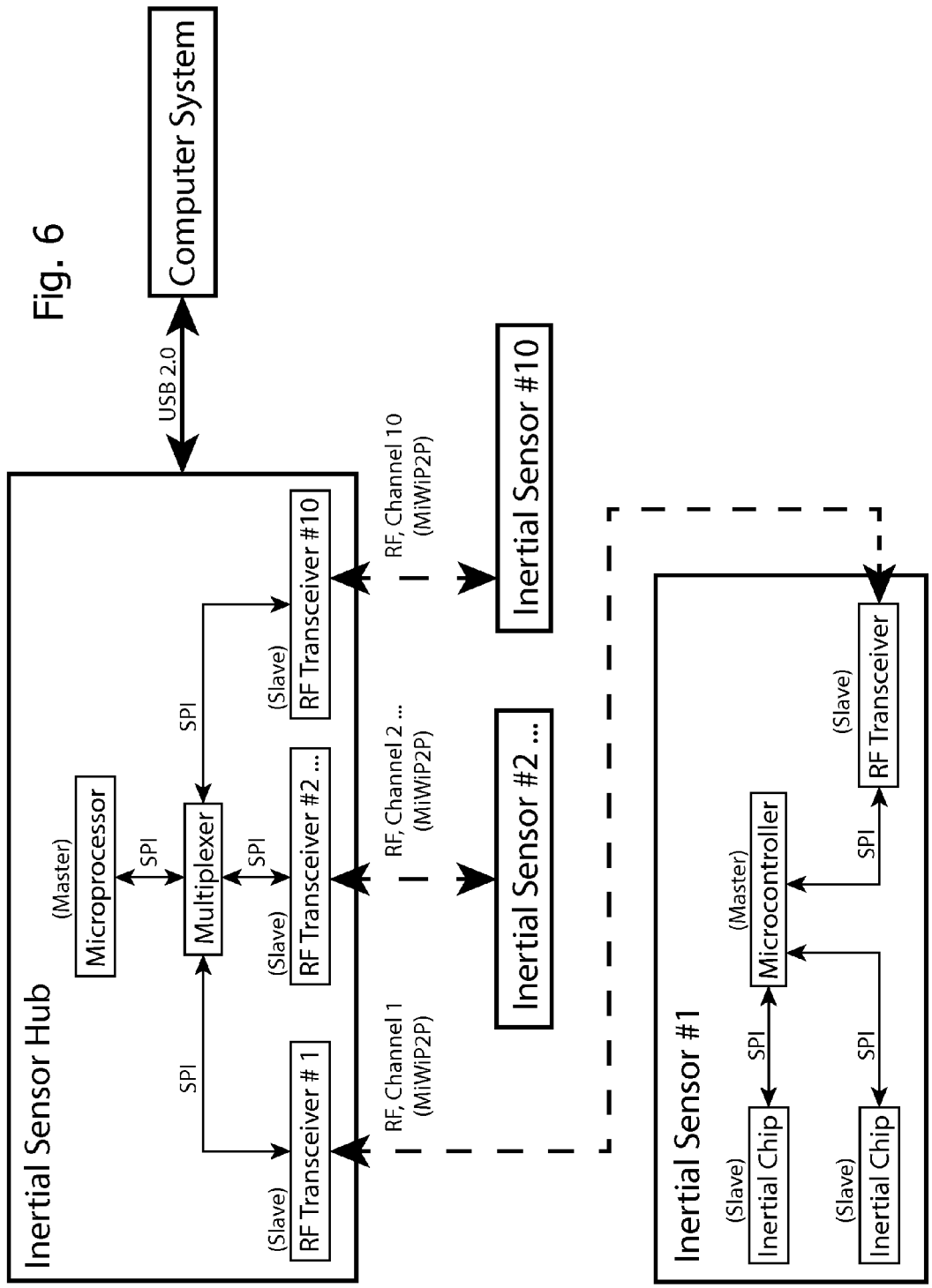
FIG. 6 shows an overview of the major circuit elements that are used to construct the inertial sensors and the inertial sensor hub.

Shown in FIG. 6, the present embodiment of the invention takes data from two ADIS16354 chips to construct one complete inertial sensor. Alternate embodiments of the invention use more than two six-degree-of-freedom inertial chips to construct an inertial sensor. Also, one six-degree-of-freedom inertial chip could be used to construct a complete inertial sensor in another embodiment of the invention if improvements in inertial sensor technology are made.

Seen in FIG. 6, the major circuit components of a complete inertial sensor comprise two inertial chips, a microcontroller, and an RF transceiver. The microcontroller issues instructions to the inertial chips and collects the raw data from them via SPI communication protocols. The data is temporarily stored on the microcontroller's internal memory before it is sent to the RF transceiver via another SPI protocol. The microcontroller acts as the master device in all SPI communications, with the peripheral chips acting as slaves. In the present embodiment of the invention, the microcontroller used is the PIC24FJ256 GB110, manufactured and sold by Microchip Technology. The RF transceiver on the inertial sensor then wirelessly sends the data to a counterpart RF transceiver aboard the inertial sensor hub via a MiWiP2P communication protocol. The RF transceiver used in the present embodiment of the invention is the MRF24J40MA, manufactured and sold by Microchip Technology. In an alternate embodiment of the invention, additional memory is incorporated into the inertial sensor's circuit to assist in buffering the data streaming to the RF transceiver. In this alternate embodiment, a multiplexer is used to share one SPI port on the microcontroller with the two inertial chips. The inertial sensor has its own battery that powers the circuit.

Also in FIG. 6 an inertial sensor hub is depicted, whose major circuit components include ten RF transceivers and a microprocessor. The RF transceivers are used to receive data from the individual inertial sensors on multiple RF channels simultaneously. The RF transceivers send this data to the microprocessor via SPI protocols. The inertial sensor hub also utilizes the MRF24J40MA for its RF transceivers. The microprocessor then sends the data to the computer system via a USB 2.0 communication protocol. The microprocessor acts as the master device in the SPI protocols, and the RF transceivers act as slaves. The microprocessor used in the current embodiment of the invention is the ADSP-BF548, manufactured and sold by Analog Devices. The USB connection to the computer system powers the circuitry of the inertial sensor hub. In an alternate embodiment of the invention, additional memory is present in the inertial sensor hub's circuitry to buffer the large amount of data from the RF transceivers, and to assist in computations performed by the processor. In this alternate embodiment, a multiplexer is used to share SPI ports on the microprocessor with the RF transceivers.

Additional circuitry is present on the pointer device, which is used to capture data from the push buttons and wirelessly send it to the computer system. The ligament balancer also has additional circuitry that captures data from its force transducers and wirelessly transmits it to the computer system as well.

In the present embodiment of the invention, the integration, quaternion, and kalman filter algorithms for all inertial sensor data is implemented on the inertial sensor hub's microprocessor, before being sent to the computer system. The advantage of this configuration is that it frees up processing power on the computer system. In alternate embodiments of the invention, the integration, quaternion, and kalman filter algorithms are distributed on the individual inertial sensors' microcontrollers, and also the algorithms are implemented directly on the computer system.

There are numerous configurations of communications protocols and circuitry that could be used in various other embodiments of the invention. All of the embedded hardware is coded in Assembly Language and C.

Operation

Figure 7:
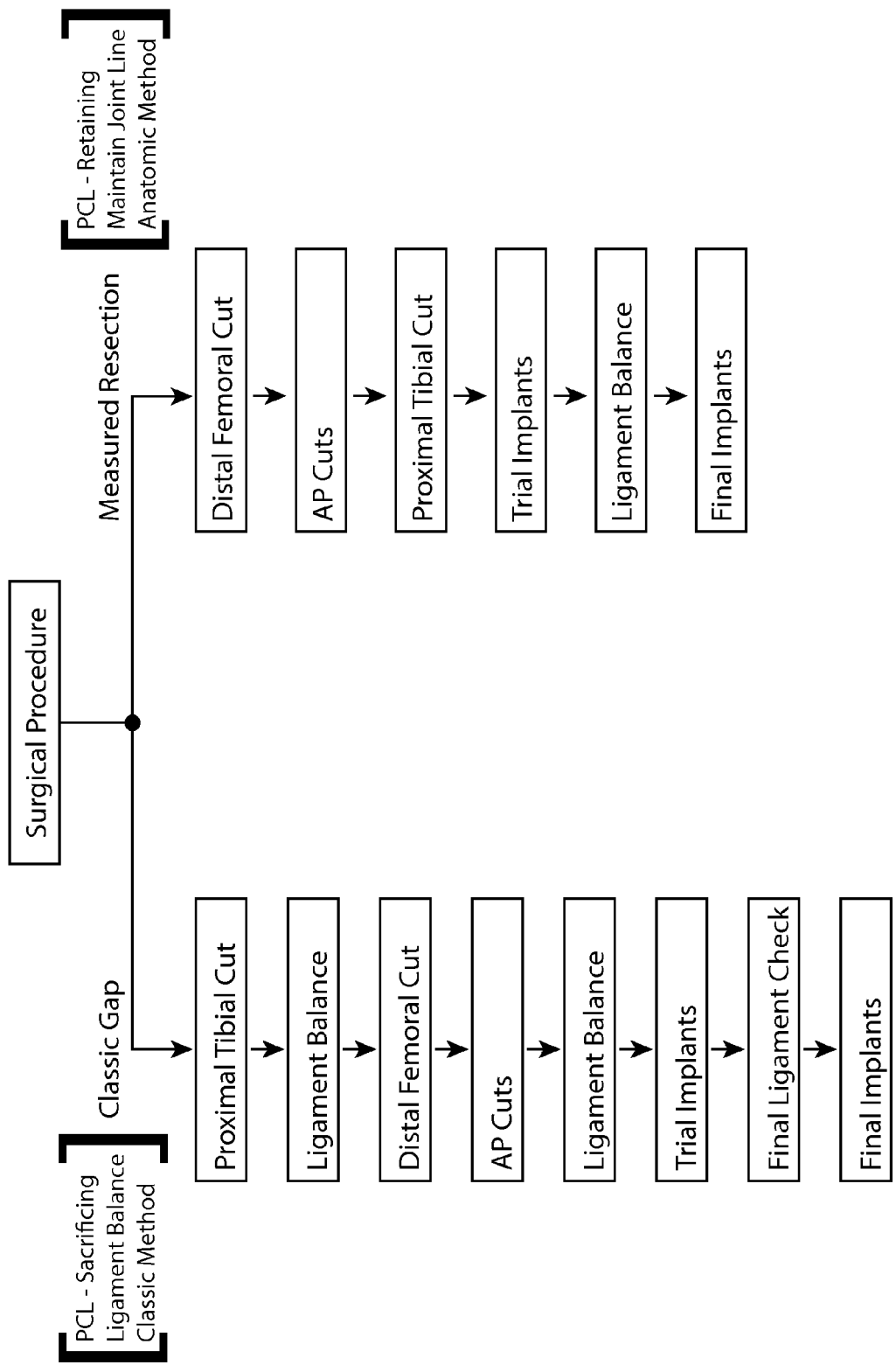
FIG. 7 shows a flowchart depicting the two most common methods of knee replacement surgery.

Before the actual operation of the surgical navigation system begins, the surgeon must first choose his or her method of surgery. Seen in FIG. 7, the user interface allows the knee replacement procedure to be programmed to either follow the measured resection approach or the classic gap approach. The measured resection approach is associated with PCL-retaining prostheses, maintaining the joint line, and using the anatomic method of placing cuts. In this approach the distal femoral cut is placed first, followed by the AP cuts, followed by the proximal tibial cut. Ligament balancing occurs after the trial components have been implanted in the joint. Alternatively, the classic gap approach is associated with PCL-sacrificing prostheses, ligament balancing, and the classic method of placing cuts. In the classic gap approach, the proximal tibial cut is placed first, followed by the distal femoral cut, followed by the AP cuts. Ligament balancing occurs after the proximal tibial cut has been placed, again after all of the surgical cuts have been made, and finally after the trial components have been installed as well. The software defaults to the classic gap approach.

The actual operation of the surgical navigation system begins with a calibration procedure. Before each surgery, the calibration box 30 shown in FIG. 4 is placed near the operating table on a flat surface and held perfectly still. The surgeon then initiates calibration of the inertial sensors via the user interface on the computer system. Shown in FIG. 1, the computer system 10 then issues commands through the inertial sensor hub 50, zeroing the individual inertial chips on board each inertial sensor.

Once calibration is complete, the tibiofemoral inertial sensors can be secured directly to the femur and tibia. Shown in FIG. 2, the tibiofemoral inertial sensors 20 are secured either using cortical pins 21 via a cortical pin flange 22, or by using a bone screw 23, bone grip fixation tool 24, and bone grip fixation flange 26.

Once the tibiofemoral inertial sensors have been secured to the bones, the user interface guides the surgeon through the determination of the hip joint center. Shown in FIG. 8, the user interface instructs the surgeon to rotate the lower extremity through an arc of motion. Internally as the surgeon rotates the leg, the computer system plots the successive position and orientation coordinates from the tibiofemoral sensor onto an internal three dimensional map. The data captured during the arc of motion forms a cloud of points resembling the surface of a sphere. The computer system then calculates the common radius to these points, which is effectively the center of the hip. Determining the hip joint center in this manner has many advantages over the conventional method of surgery using an intramedullary rod. Aside from being far less invasive than the intramedullary rod, the inertial sensor based method is also more accurate. The intramedullary rod uses the anatomic axis of the femur to determine the center of the hip joint. The anatomic axis of the femur has been shown by studies of cadavers to be between five and seven degrees off of the mechanical axis along which the center of the hip joint lies. This relationship between the anatomic axis and the center of the hip joint may not hold true for everyone however. If a patient's femur happens to be a statistical outlier, or has been warped from a prior accident, there is little that can be done in conventional surgery to determine the center of the hip joint with certainty. The inertial based surgical navigation method by contrast is guaranteed to determine the center of the hip joint by using the center of rotation of the joint as its means of determination. Further discussion of how the joint centers are used internally by the computer system is presented in the software section.

Next the user interface guides the surgeon through the determination of the ankle joint center. Shown in FIG. 9, the foot strap 70 is secured to the foot, and the foot is also rotated through an arc of motion. Similar to the hip joint center calculation, the inertial sensor attached to the foot strap also generates a cloud of points. The common radius for the cloud of points is used in part to determine the center of the ankle. Additionally, the surgeon maps anatomical landmarks around the ankle joint with the pointer device to provide more data for the ankle joint center calculation. Additionally, the anatomical landmarks are used to reconstruct a three dimensional map of the tibia as explained in the software section. To be clear, anatomical landmarks are generally accepted structures of human anatomy used as references, in the case of knee replacement surgery, to align cutting instruments and implants. In point mapping, the tip of the pointer device is held against a particular anatomical landmark. A button is pressed on the pointer device and the position and orientation coordinates from the tip are saved into memory. Henceforth the computer system, by means of the inertial sensor attached to the bone, is able to track the position and orientation of the anatomical landmark of interest. After the anatomical landmarks around the ankle have been registered and the ankle joint center calculation is complete, the surgeon then removes the foot strap.

Figure 10:
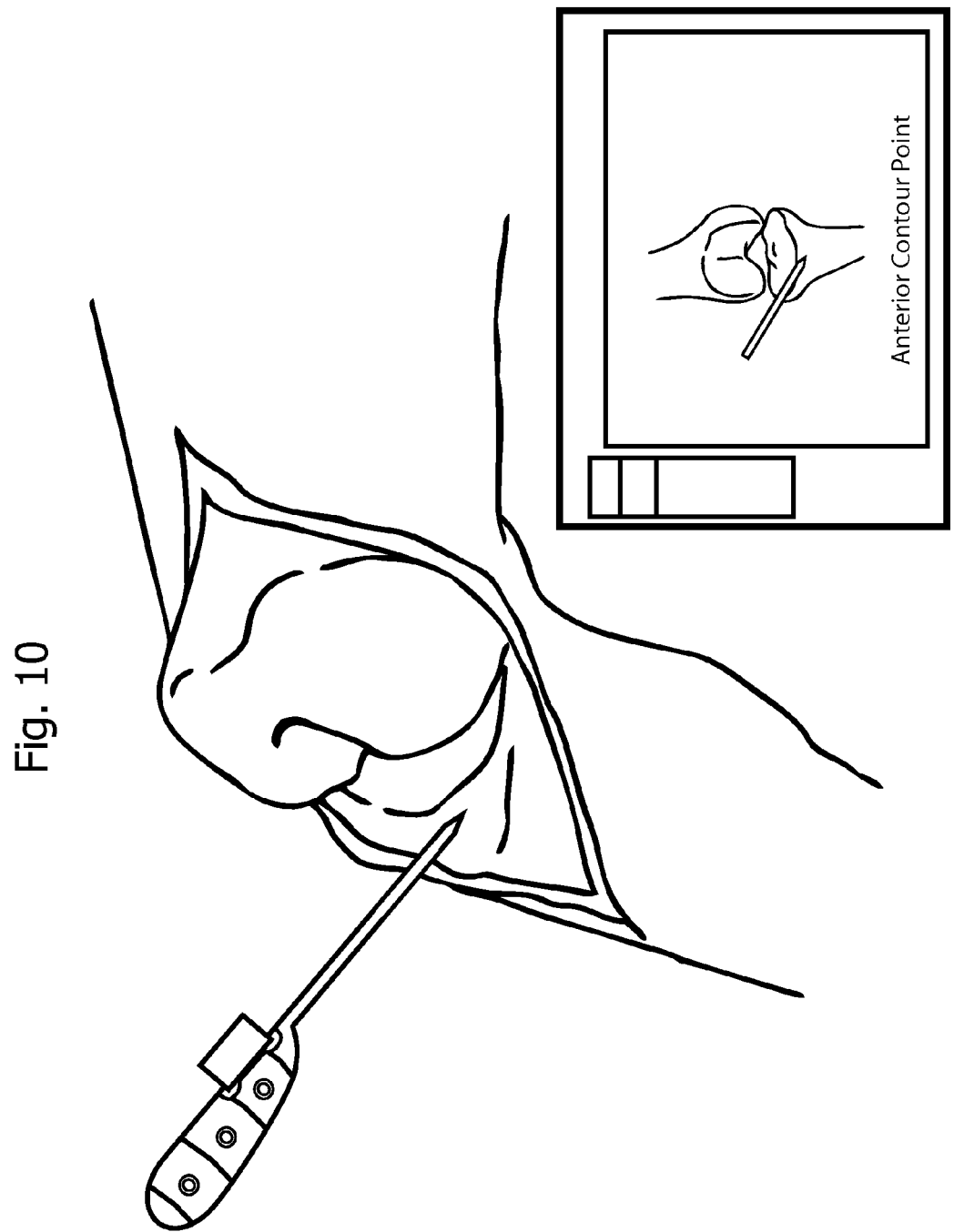
FIG. 10 shows the registration of an anatomical landmark of the knee, and the accompanying screenshot from the graphical user interface.

The next step of the procedure is to determine the center of the knee. Shown in FIG. 10, the computer then prompts the surgeon to register various anatomical landmarks, surfaces, and axes located in and around the knee joint with the pointer device. The specific anatomical landmarks, surfaces, and axes are registered one at a time and are discussed in greater detail in the software section. To map a surface of bone, the tip of the pointer device is carefully scratched along the surface of interest and a button is held down to save the position and orientation coordinates for the set of points that comprise the surface into memory. To map an axis, the length of the pointer device is held down longitudinally against the bone along the imaginary line on which the axis runs. A button is pressed and the position and orientation of the axis is saved into memory. In both cases, the computer system then tracks the position and orientation of the surface or axis of interest by means of the inertial sensor attached to the bone. The computer also instructs the surgeon to move the knee through its flexion arc and rotate the tibia internally and externally. The data generated from these motions, as well as the registered knee geometry is used to calculate the knee joint center.

Figure 11:
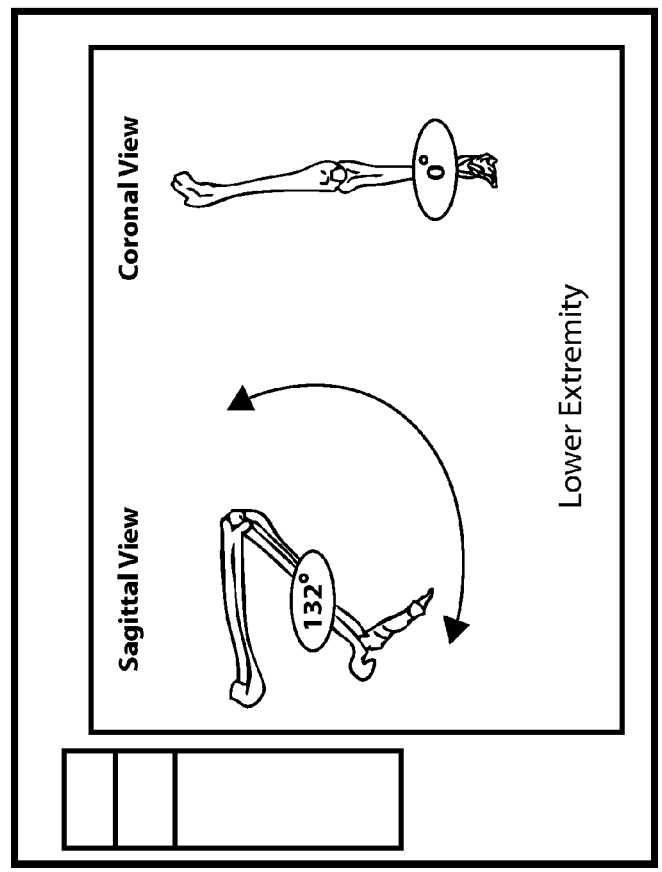
FIG. 11 shows a visualization of the lower extremity that is used to quantify the extent of deformity throughout the flexion are shown by the graphical user interface.

Once all of the joint center calculations are complete and the anatomical landmarks, surfaces, and axes have been registered, the computer system can create a model of the lower extremity that tracks the position and orientation of the femur and tibia in real time. Shown in FIG. 11, this model is used to quantify the extent of any varus/valgus deformity through the flexion arc. The surgeon then uses this information to make initial soft-tissue releases around the knee joint. Further discussion of how this model is generated is presented in the software section.

Next, the surgeon is ready to make the proximal tibial cut. The computer system by this step in the procedure has all of the information that it needs to calculate the optimal cutting planes for the surgical cuts. Seen in FIG. 12, the user interface provides guidance for the surgeon as to how to place the tibial cut guide relative to the optimal cutting plane. The user interface displays the difference in the coronal angle, sagittal angle, and distal/proximal distance between the cut guide's actual cutting plane and the optimal cutting plane calculated by the computer system. The numerical data regarding the position and orientation of the cut guide's cutting plane is updated in real time on the monitor as the surgeon moves the cut guide. The movement of the cut guide's cutting plane is also visually displayed on the monitor, juxtaposed against a static image of the optimal cutting plane. The two planes are displayed as lines on the computer screen, seen from both the coronal perspective and the sagittal perspective. Like a computer game, the goal for the surgeon is to align the two planes in both of the perspectives being displayed. The surgeon uses the numerical and visual information to initially pin the base of the tibial cut guide to the bone, such that its cutting plane is in relatively close alignment to the optimal cutting plane. A button on the user interface lets the computer system know that coarse alignment of the cut guide has taken place and that its base is pinned to the bone. While still displaying the juxtaposition of the two planes, the computer system then instructs the surgeon to turn the fine adjustment screws in 90 degree increments to make further adjustments to the coronal angle, sagittal angle, and distal/proximal location of the cut guide's cutting plane, such that the two planes are fully aligned. The tibial insertion piece and cut guide inertial sensor are then removed from the tibial cutting slot as the cut guide is now in full alignment with the optimal cutting plane. The proximal tibial cut is then made and the cut check tool is used to verify the actual plane of the cut bone.

After the proximal tibial cut has been made, the surgeon then uses the ligament balancer to assess ligament tension in the medial and lateral compartments of the knee. Seen in FIG. 13, the user interface displays force measurements from the force transducers built into the ligament balancer. The ligament balancer is used to assess the ligament tension of the knee in both full extension and at 90 degrees of flexion. Additional soft-tissue releases may be necessary at this step in the procedure.

Figure 14:
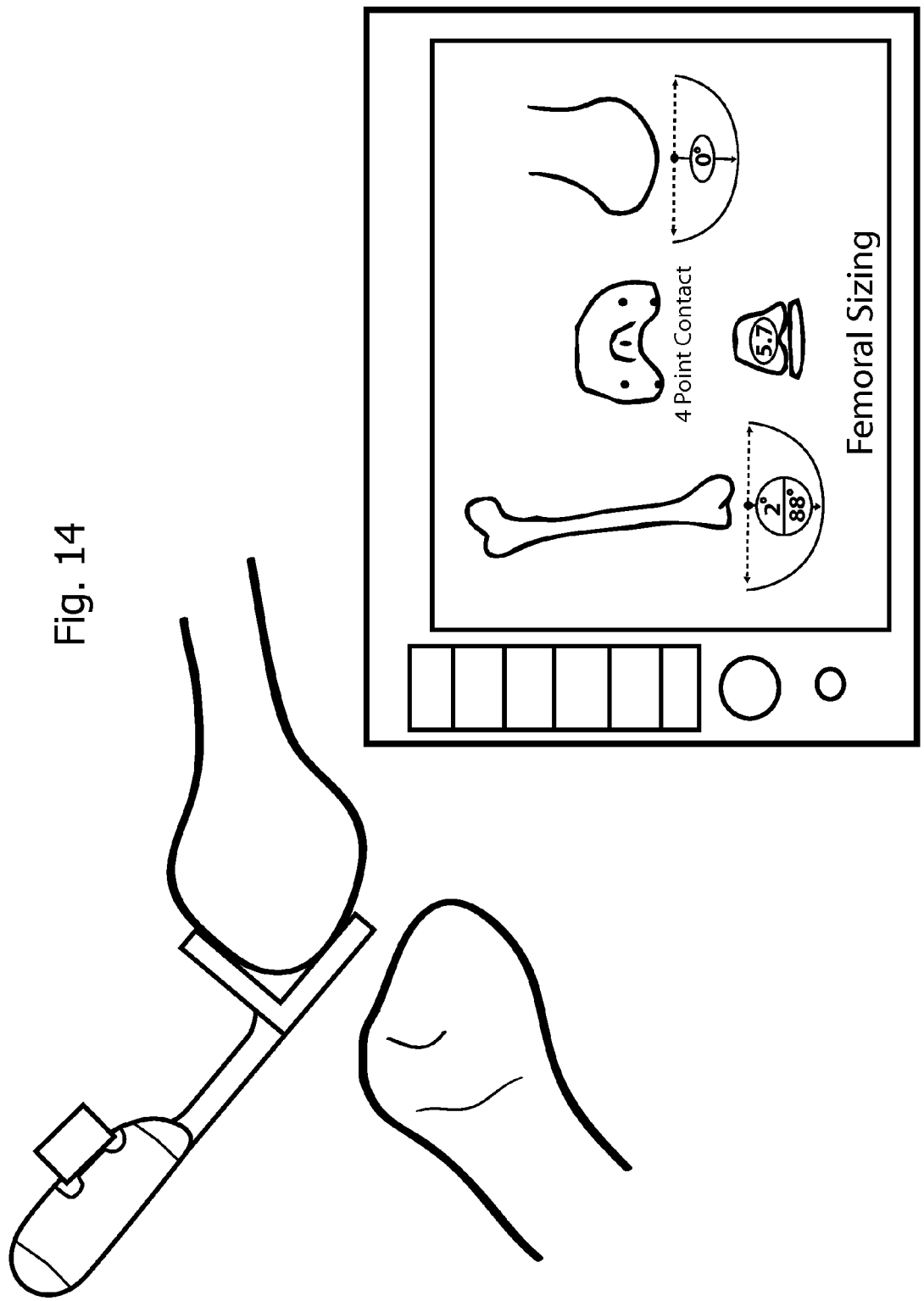
FIG. 14 shows the femoral sizing tool being inserted into the knee and the accompanying screenshot from the graphical user interface.

Next, the user interface prompts the surgeon to ascertain the size of the femur with the femoral sizing tool. Shown in FIG. 14, the tool is inserted into the knee joint at 90 degrees of flexion with the L-shaped head pressed against the most distal and posterior points along the surface of the femur. Once the data is taken and entered into the computer system, the surgeon is ready to begin femoral cut planning.

Femoral cut planning is the process whereby the surgeon plans out exactly the planes along which the distal femoral cut and AP cuts will take place. Femoral cut planning cannot be completely outsourced to the computer system because there are many trade-offs involved in the positioning of the femoral component that only a trained surgeon is qualified to understand. These trade-offs occur in large part because the femoral component often does not match the exact size of the patient's femur. For example, when implanting a slightly oversized femoral component the extra length of the component must either be displaced to the anterior or posterior aspect of the femur. If the femoral component is displaced in the anterior direction, there may be a risk in notching the anterior cortex of the femur. If the femoral component is displaced in the posterior direction, the patient may later feel discomfort when flexing his or her knee. Trade-offs such as this one illustrate why cut planning is an important part of the surgical procedure. Though the computer system cannot automatically calculate the optimal cutting planes for the femoral cuts, it can assist the surgeon by simulating what some of the preferred surgical cuts might look like if made to the femur.

Figure 15:
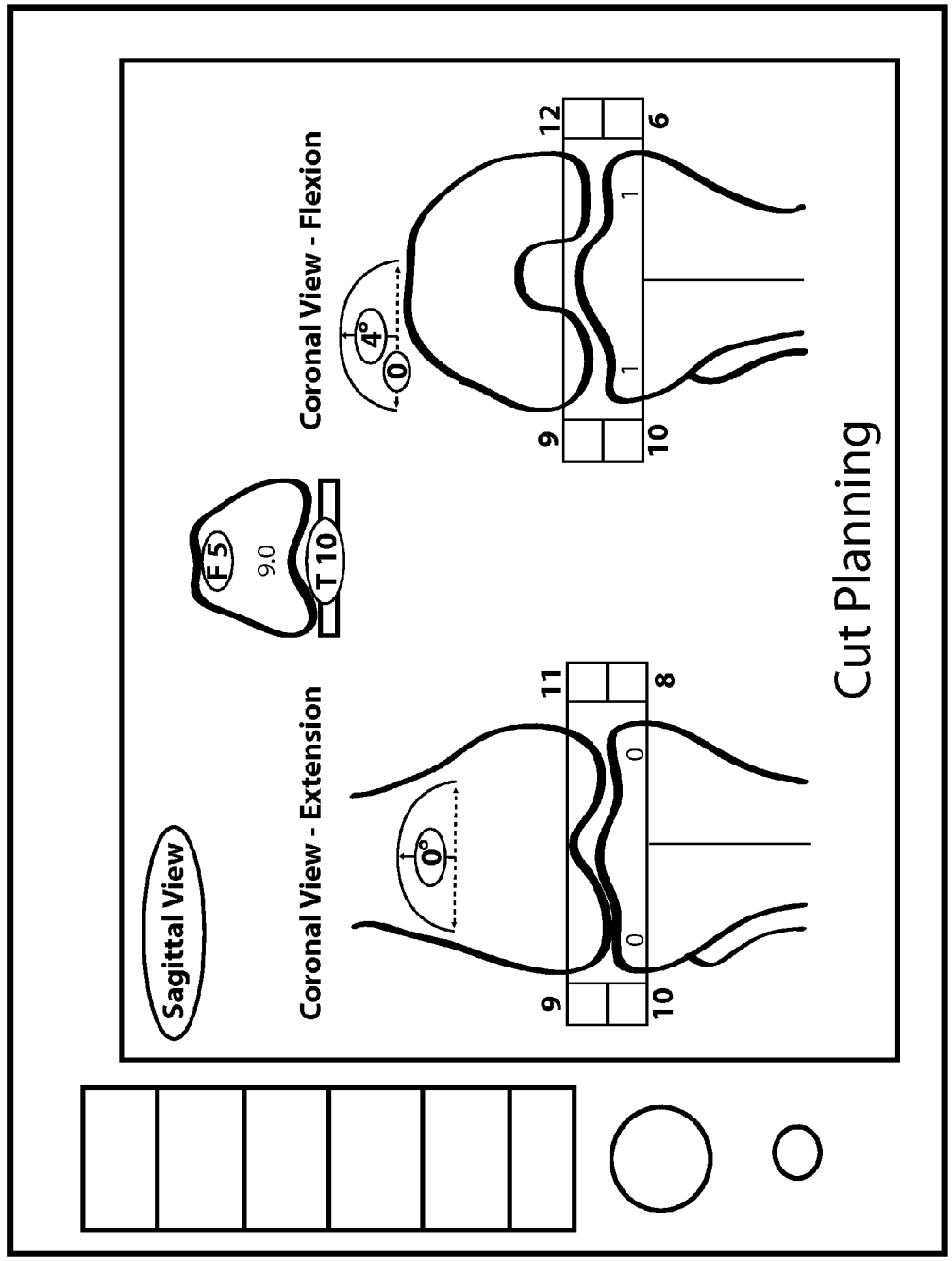
FIG. 15 shows the femoral cut planning screen.

FIG. 15 depicts the femoral cut-planning screen of the user interface that is used in the present embodiment of the invention. Using the femoral cut planning screen, the surgeon can see what happens if the cutting planes are moved in the anterior/posterior direction, the distal/proximal direction or if the coronal, sagittal, or transverse angles of either the distal femoral or AP cuts are altered. Specifically the cut planning screen displays numerical values for the distal/proximal position of the distal femoral cutting plane and the anterior/posterior position of the AP cutting planes, by quantifying the amount of bone being resected in each direction. The coronal, sagittal, and transverse angles of the cuts are also displayed on the cut planning screen and are quantified with respect to specific anatomical landmarks, surfaces, and axes. The cutting planes are also visually displayed as lines juxtaposed against the femur. In planning the distal femoral cut, the femur is shown in full extension with the all of the cutting planes juxtaposed against it from both the coronal and sagittal perspectives. In planning the AP cuts, the femur is shown in 90 degrees of flexion with all of the cutting planes juxtaposed against it from both the coronal and sagittal perspectives. When the distal femoral cut is being planned, the AP cut planning is minimized to one corner of the screen. When the AP cuts are being planned, the distal femoral cut planning is minimized to one corner of the screen. The user interface is also able to simulate what the surgical cuts will look like if the size of the femoral or tibial component is changed. The system is tremendously flexible, because the user interface is able to perform these simulations intra-operatively. In conventional surgery by comparison, cut planning is usually performed before the operation and is notoriously unreliable. Making an intra-operative comparison to conventional surgery, the surgeon is forced to judge many distances and angles by eye as the tools are simply not present to precisely quantify the position and orientation of the cutting planes in three dimensions.

Once the cut planning is completed, the surgeon is then ready to make the distal femoral cut. Shown in FIG. 16, the base of the distal femoral cut guide is placed in close proximity to the optimal cutting plane determined in the previous step. Like the proximal tibial cut guide's navigation, the user interface displays the difference in the position and orientation of the cut guide's actual cutting plane and the optimal cutting plane. The surgeon uses this numerical information as well as the visual cues from the user interface to pin the base of the cut guide to the bone. Once the base of the distal femoral cut guide is pinned into place, fine adjustment screws on the cut guide are used to further fine-tune the distal/proximal location and the coronal and sagittal orientation of the cutting slot. The distal femoral insertion piece with the cut guide inertial sensor attached is removed from the cutting slot, and the surgeon then makes the distal femoral cut. After the distal femoral cut is completed, the surgeon then checks the accuracy of the cutting plane with the cut check tool.

Next the AP cuts are made. Shown in FIG. 17, the AP cut guide is navigated to the optimal cutting plane determined in the femoral cut-planning screen. The AP cut guide has no fine adjustment screws, and so is pinned in as close alignment as possible to the optimal cutting plane. For AP cut guide navigation, the user interface displays the anterior/posterior position and the transverse angle of the cut guide in relation to the optimal cutting plane. The transverse angle is quantified with respect to the three most commonly used axes for AP rotation, the epicondylar axis, the posterior condylar axis, and whiteside's line. Once the AP cut guide is pinned into place, the AP cuts are made. The cut check tool is then used to verify the planes of the AP cuts.

A patellar cut may be necessary, however the patellar cut is not navigated by the inertial based surgical navigation system. The patella is a small bone surrounded by soft-tissues and the act of navigating the cut may be more harmful to the bone than beneficial. The patellar cut is made using traditional instrumentation.

After all of the surgical cuts have been made, the surgeon then inserts the ligament balancer into the knee joint again and measures the ligament tension. The ligament balancer is used to measure the ligament tension of the knee at full extension and at 90 degrees of flexion. Additional soft-tissue releases may be necessary at this time. The surgeon also checks to see that the flexion gap, or the gap between the cut surface of the tibia and the cut surface of the posterior femur, is equivalent to the extension gap, or the gap between the cut surface of the tibia and the cut surface of the distal femur. If the distance between the gaps is not equal the surgeon may have to adjust the surgical cuts accordingly. If the distance between the flexion and extension gaps is equal, and the ligament tension is balanced across the joint, the surgeon can proceed.

Figure 18:
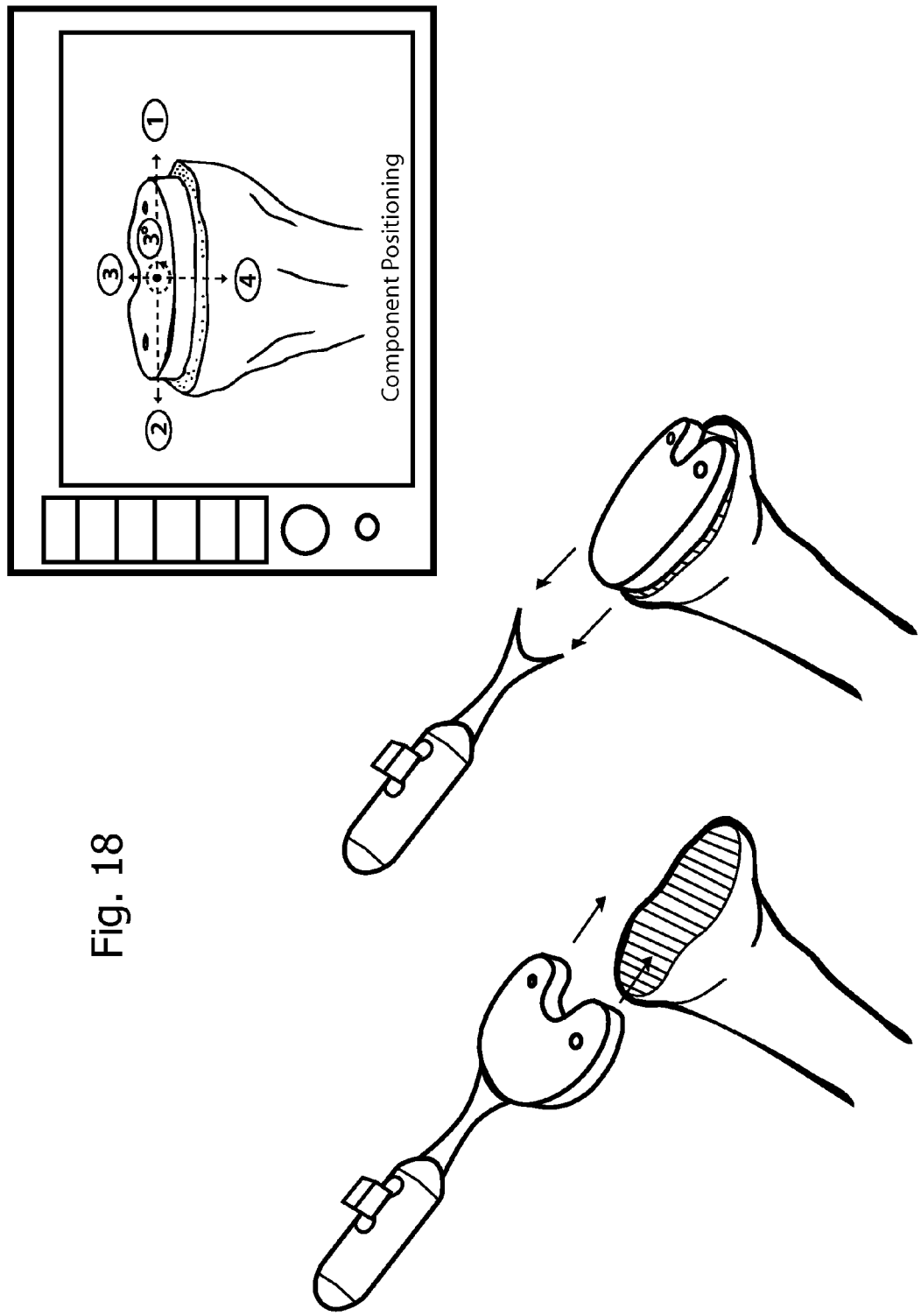
FIG. 18 shows the trial tibial component being navigated to its optimal position and orientation and the accompanying screenshot from the graphical user interface.

Finally, the trial components are implanted into the bones. The computer system has the information necessary at this step in the procedure to calculate the optimal position and orientation for both the femoral and tibial components. Component navigation works much the same way as cut guide navigation. FIG. 18 shows the trial tibial component being navigated on the cut surface of the tibia. The trial tibial component is attached to the tibial implant tool, which tracks the component's position and orientation. The user interface displays numerical values for the anterior/posterior position, the medial/lateral position, and the transverse angle of the tibial component relative to its optimal position and orientation. These numerical values update in real time as the component is being moved. The user interface also visually displays stationary planes along the anterior/posterior axis and the medial/lateral axis juxtaposed against an isometric image of the cut tibia. The planes form a static three dimensional cross-hair which represents the optimal position and orientation for the component. To navigate the component, the user interface also displays a second three dimensional cross-hair juxtaposed against an isometric image of the tibial component, whose position and orientation on the computer screen moves in real time as the surgeon navigates the actual tibial component. The goal for the surgeon is to align the cross-hair representing the tibial component, with the cross-hair representing the optimal component position and orientation. Once the trial tibial component is aligned to the correct position and orientation, the trial tibial component is fixed to the bone and the tibial implant tool releases the trial component. The navigation of the trial femoral component works in the same manner. When guiding the femoral component, the user interface only displays visual cues and numerical values for the medial/lateral position of the component as the other parameters are predetermined by the femoral cuts. With the trial components implanted, the knee is run through its full range of motion and the ligament tension is assessed. If the knee is moving correctly and the ligament tension is well balanced, the trial components are removed and the final components are navigated into position and implanted.

In an alternate embodiment of the invention, a robot performs the various steps of the procedure instead of a human.

Software

Figure 19:
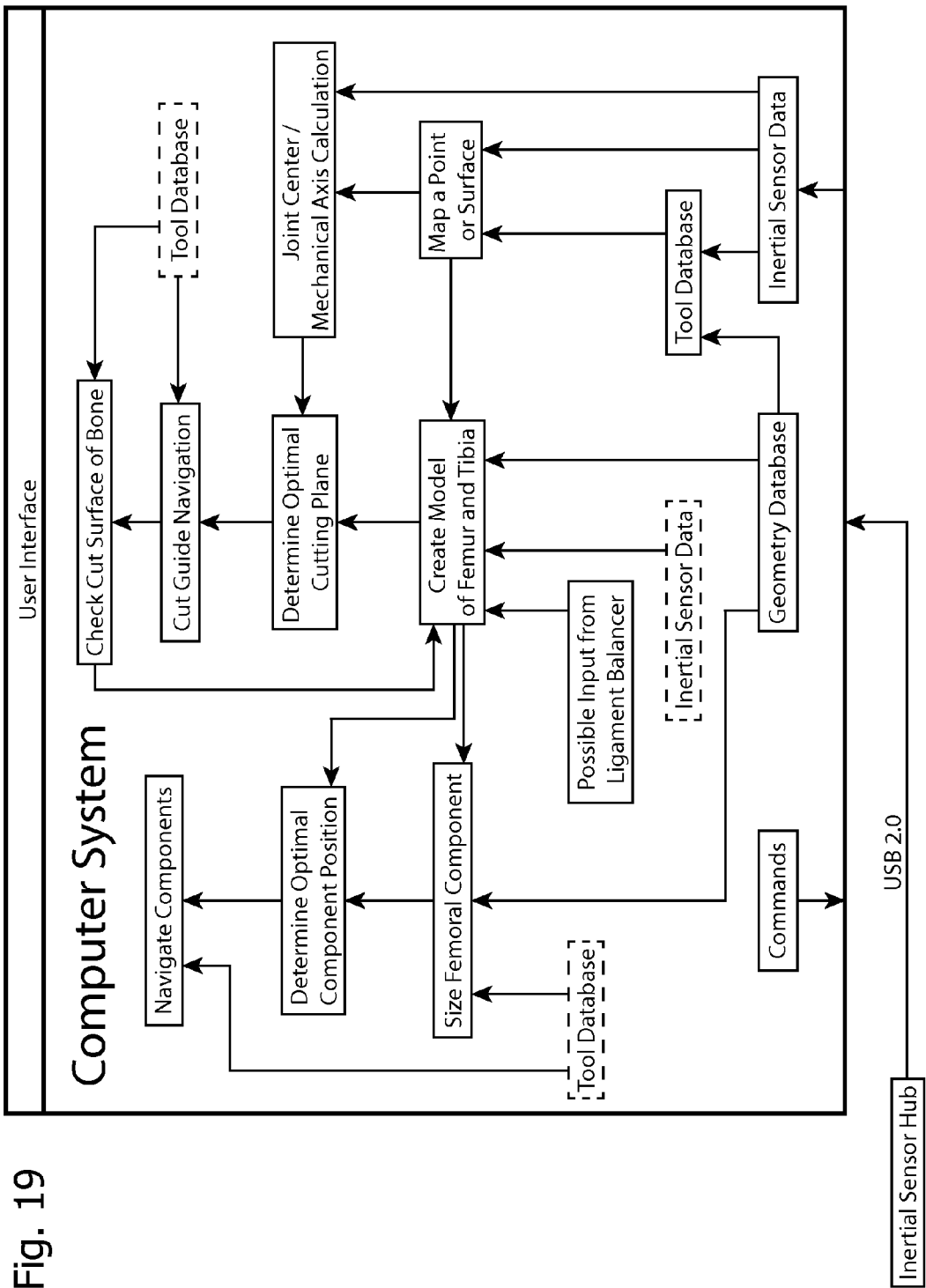
FIG. 19 shows a flowchart containing all of the major software functions of the computer program.

FIG. 19 depicts a software flow chart for the computer program run by the surgical navigation system. Each box in the flowchart represents a software function. The lower level functions shown in the flowchart comprise the fundamental building blocks from which the program is built. Data from the lower level functions are used to build the mid-level and high-level functions. As the functions move upward in the flowchart, the complexity of the software increases. Finally, at the top of the flowchart, the computer system draws upon information from all of the various functions to create a user interface which the surgeon interacts with.

At the lowest level of the flowchart shown in FIG. 19, commands are direct instructions issued to the inertial sensor hub and the inertial sensors. The commands primarily are concerned with accessing the individual registers aboard the inertial chips and writing commands that zero the inertial chips during the initial calibration stage of the procedure.

Also in FIG. 19 at the lowest level of the flowchart, a geometry database is preloaded with CAD data for all of the surgical tools and implants. This CAD data allows the computer to reconstruct the dimensions for all of the instrumentation inside of a common coordinate system within the program. The geometry database is also preloaded with the geometric reconstructions of numerous femurs and tibias taken from cadavers. The cadaveric lower extremity data is used in part to reconstruct a model of the actual femur and tibia being operated upon.

FIG. 19 also illustrates inertial sensor data at the lowest level of the flowchart. The inertial sensor data is the processed provided by the inertial sensor hub. This data includes the position and orientation coordinates of each inertial sensor, as well as information from various other registers within the inertial chips such as the status of the internal circuitry. The computer system decodes this data into a useable format for the rest of the software functions.

Moving up in the flowchart shown in FIG. 19, a tool function is created from the geometry database and from the inertial sensor data. Using the pointer device as an example, from the geometry database the specific dimensions of the pointer device is known. From the inertial sensor data, the position and orientation of the instrument inertial sensor attached to the pointer device is known. The tool function combines the two sets of information to track specifically the position and orientation of the tip of the pointer device. In the case of the cut check tool, the two sets of information are combined to track the plane along the head of the tool. In other words, the tool function uses dimensional data and inertial sensor data to track the position and orientation of specific geometry of interest for each tool used in the surgery.

Moving up further still in the flowchart depicted in FIG. 19, point, surface, and axis mapping of the lower extremity becomes possible. In particular the pointer device 40 and the tibiofemoral inertial sensors 20 shown in FIG. 1, play a key role in mapping points, surfaces, and axes. In point mapping, the tip of the pointer device is held against a point of interest, which is usually an anatomical landmark. From the tool function, the position and orientation of the tip of the pointer device is known. At the instant in time when the anatomical landmark at the tip is saved into memory, the point of interest is then transformed by the movement of the tibiofemoral inertial sensor attached to the bone on which the point was taken. For example, suppose that the computer system prompts the surgeon to register a point located on the tibia. Prior to the point registration, the computer system tracks the position and orientation of the tip of the pointer device. At the exact instant of point registration, the computer system saves the position and orientation coordinates of the tip of the pointer device into memory. Immediately following the point registration, the saved point is then mathematically transformed by the position and orientation movement that the tibia experiences, which is known by means of the tibiofemoral inertial sensor attached to the bone. In this manner the position and orientation of registered points along the surface of a bone can be tracked in real time relative to the tibiofemoral inertial sensor. The tracking of points is essentially a software process, and is dependent upon the surgeon correctly positioning the tip of the pointer device in exactly the location of the anatomical landmark of interest at the instant of point registration. Similarly, when a surface or axis is registered, the position and orientation of the geometry relative to the tibiofemoral inertial sensor is saved into memory and is then immediately mathematically transformed by any subsequent movement of the bone. Mapping points, surfaces, and axes plays a crucial role in reconstructing the geometry of the lower extremity within the computer system, and ultimately in calculating the optimal cutting planes and implant positions and orientations used for total knee replacement surgery.

In FIG. 19 across from point mapping, a model of the femur and tibia is constructed. This model is created from the mapped anatomical landmarks, surfaces, and axes as well as from the inertial tracking data and the dimensional data taken from cadavers extracted from the geometry database. To be clear, the mapped anatomical landmarks, surfaces, and axes are used recreate the critical geometry of the two bones that the computer system relies upon for the high level calculations of the optimal cutting planes and the optimal prosthesis position and orientation. The inertial sensor data is used to track specifically the motion of the critical geometry as the knee is moved throughout the surgery. Finally the geometry database uses dimensional information taken from cadavers to fill in the non-critical geometry of the two bones. The result is a visual representation of the position and orientation of the femur, tibia, and critical geometry of the bones that is tracked in real time. The model can also be supplemented with data from the force transducers 172 on the ligament balancer 170 seen in FIG. 3. The model of the femur, tibia, and critical geometry is extremely useful because it allows for the simulation of the surgical cutting planes being considered before they are actually applied to the two bones. This information is also used to visualize how the femoral and tibial implants will be positioned on the two bones, before any cuts are even made. The surgeon can use this information to plan the surgical cuts intra-operatively, navigate the individual cut guides, and navigate the implants with great precision and accuracy.

Above point mapping in the flowchart in FIG. 19, the position and orientation of the joint centers of the hip, ankle, and knee are determined. The software uses a combination of data including the mapped points, surfaces, and axes as well the tracking data from the inertial sensors to calculate the position and orientation of the geometric centers of each joint. The position and orientation of the joint centers are tracked in real time, and are in turn used to reconstruct the position and orientation of the mechanical axis of the lower extremity. The mechanical axis runs through several bones, and near the hip joint is embedded in thick layers of muscle and fat making it impossible to map directly with the pointer device. The mechanical axis is a critical geometric construct that is used by surgeons to determine the extent of knee deformity, and is also used to determine the optimal cutting planes along which the surgical cuts should be made. Previously in conventional surgery, the traditional way to determine the mechanical axis was to drill a hole in the knee, ream out the intramedullary canal, and place an intramedullary rod into the knee, which is highly invasive by comparison.

Across from the joint center functions in the flowchart in FIG. 19, the optimal cutting planes for the surgical cuts are determined. The cutting planes are calculated by geometry taken from the model of the femur and tibia, as well as geometry derived from the joint centers and mechanical axis of the knee. Specifically, the cutting planes for the proximal tibial cut, distal femoral cut, and AP cuts are determined. The cutting planes are calculated for both the anatomic method of placing cuts pioneered by Krackow, and for the classic method of placing cuts pioneered by Insall. The software allows the surgeon to choose the method that he or she is most familiar with. The calculations for the cutting planes also take into account the particular prosthesis that has been selected for implantation.

Above the optimal cutting plane determination in the flowchart in FIG. 19, individual cut guides are navigated to the correct position and orientation on the bone. Using the proximal tibial cut as an example and referring back to FIG. 2, the tibial insertion piece 90 with the cut guide inertial sensor attached 120 is first inserted into the tibial cutting slot 82. By means of the tool function, the position and orientation of the plane along the insertion piece is known. With the insertion piece 90 inserted into the cutting slot 82, the tool function is now effectively tracking the position and orientation of the actual cutting plane to be used for the proximal tibial cut. The computer system then runs a comparison between the position and orientation of the cut guide's cutting plane, and the position and orientation of the optimal cutting plane. The software is able to then give the surgeon numerical measurements for the distal/proximal distance as well as coronal and sagittal angles by which the two planes differ. The software is also able to offer visual cues for how to correctly place the cut guide onto the bone. Referring back to FIG. 2 again, the surgeon then pins the base 84 of the cut guide to the bone, with the cutting slot 82 relatively well aligned with the optimal cutting plane. Further adjustment of the cutting slot 82 can be made with the fine adjustment screws 86. When the two planes are sufficiently aligned, the tibial insertion piece 90 with the cut guide inertial sensor 120 still attached is removed from the cutting slot 82. The tibial cut is then made. The cut guide navigation procedure is essentially the same for the distal femoral cut and the AP cuts. The benefit of the inertial based cut guide navigation procedure is that it is significantly simpler and less invasive than the procedure associated with the large mechanical cutting jigs used in conventional surgery. The inertial based cut guide navigation procedure is streamlined into fewer steps and uses fewer parts to achieve the same goals in a more accurate and repeatable fashion. Also, inertially navigated cuts are aligned three dimensionally along multiple planes, whereas conventional jigs are usually designed to give the surgeon feedback as to only one plane. This is a significant improvement because superior alignment of the surgical cuts has been shown to contribute to implant longevity in a patient.

In FIG. 19 above cut guide navigation on the flowchart, the cut surface of bone is then double checked with a cut check tool. Seen in FIG. 3, the position and orientation of the surface of the cut check tool 130 is tracked via the tool function. The flat surface of the cut check tool is placed against the recently cut surface of the bone to measure the position and orientation of the plane along the raw surface. The computer then makes a comparison between the raw surface's plane and the optimal cutting plane. If a mistake has been made, the surgeon can attempt to correct it by placing another cut into the bone. The data from the cut bone is also used to update the model of the femur and tibia.

In FIG. 19 across from the model of the femur and tibia, a femoral sizing tool is used to determine the optimal size of the femoral component. Seen in FIG. 3, the femoral sizing tool 140 is placed against the posterior and distal aspects of the femur, with the L-shaped head 142 making solid contact against both of the femoral condyles. From the tool function, the position and orientation of the L-shaped head 142 is known. The L-shaped head is then used to ascertain the position and orientation of the posterior and distal most points on the medial and lateral condyles. The computer system then compares this information to the model of the femur already generated, as well as the data from cadaveric femurs provided by the geometry database. Using this information, the software then recommends a size for the femoral component. Without the use of any specialized tools, the computer is also able to recommend a size for the tibial component based upon the computer-generated model of the tibia.

In FIG. 19 above the femoral sizing calculation, the optimal position and orientation is determined for both the tibial and femoral components. This positioning refers to the ideal position and orientation that the final prosthesis should have on the cut surfaces of the bones. For example after the proximal tibial cut is made, the tibial component still needs to be positioned and oriented along the anterior/posterior axis of the tibia, the medial/lateral axis of the tibia, and rotationally on the cut surface of the tibia. The femoral component needs to be positioned along the medial/lateral axis of the femur. The optimal positions and orientations of the components are calculated using data taken from the model of the femur and tibia, as well as data taken from the component sizing calculations.

In FIG. 19 above the optimal component positioning, component navigation is used to navigate the femoral and tibial components to their correct position and orientation. The component navigation procedure works much like the cut guide navigation procedure. Referring back to FIG. 3 and using the trial tibial component 182 as an example, the tool function is able to track the position and orientation for both the tibial implant tool 180 and trial tibial component 182. The computer runs a comparison between the position and orientation of the trial tibial component and the optimal tibial component positioning. The software provides numerical measurements and visual cues that assist the surgeon in placing the trial tibial component in the correct position and orientation. Referring again to FIG. 3, once the trial tibial component 182 is placed in the correct position and orientation, the tibial implant tool 180 implants the component 182 into the bone and detaches from the component 182. This procedure is repeated for the femoral trial component and for the final components. Component navigation ensures that the prosthesis position and orientation will be accurate and precise, thus increasing the prosthesis longevity. None of the optical navigation systems to date navigate the tibial and femoral components on the cut surface of the bone. In conventional surgery also, the components are essentially positioned on the bone by eye, which is a far less precise method of positioning implants.

The user interface draws upon elements from all of the calculations and software algorithms present in the flowchart in FIG. 19. The user interface provides a means by which the surgeon can interact with the program and move step-by-step through the procedure deriving the benefits of inertial based surgical navigation. The interface can run a tutorial mode, educating the surgeon on how to use the navigation system, as well as take screenshots from the program itself.

Figure 20:
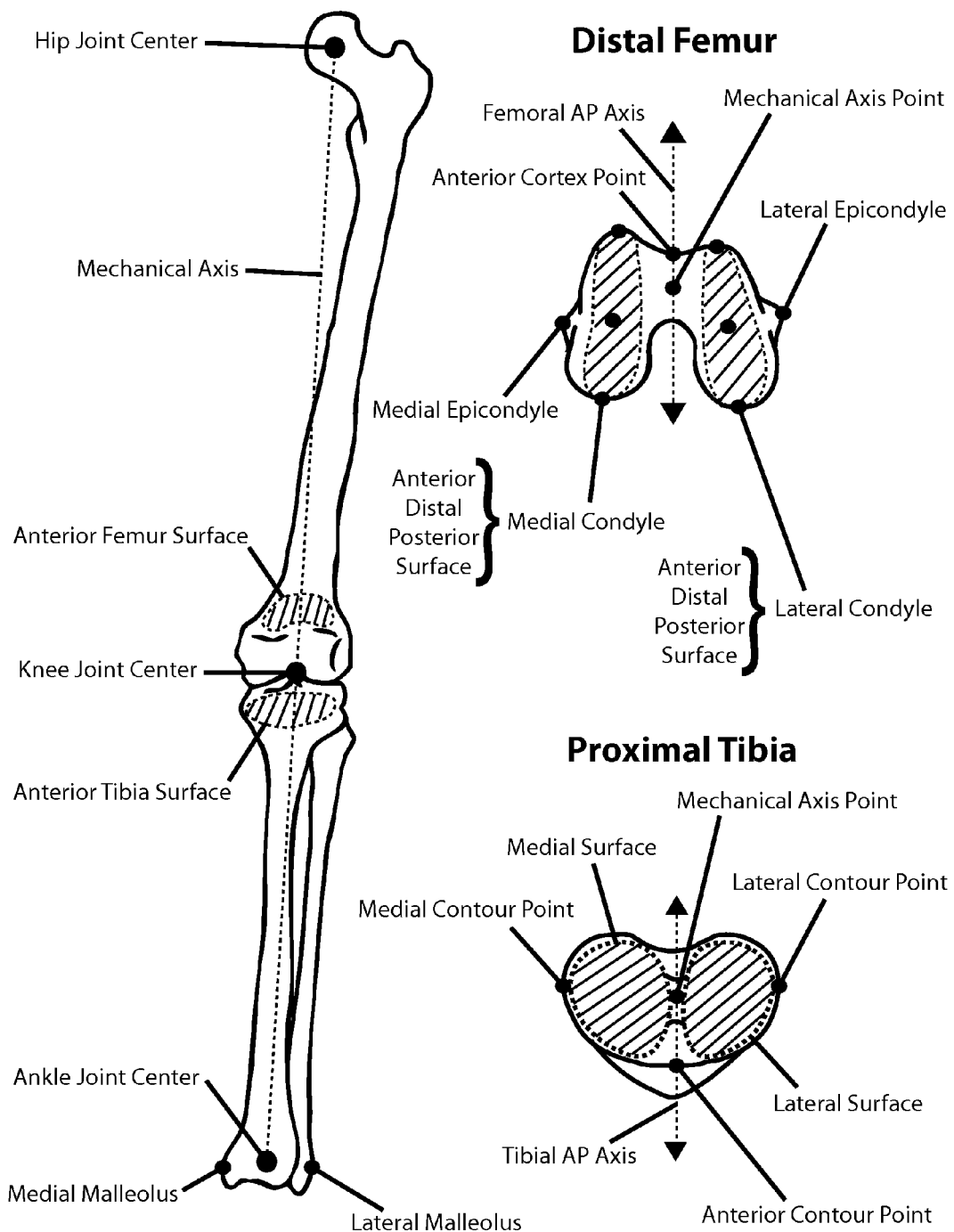
FIG. 20 shows a visualization, displayed on one of the computer monitors, of the lower extremity after all of the anatomical geometry has been registered by the pointer device.

Seen in FIG. 20, the user interface has one dedicated monitor that shows a visualization of the position and orientation of the femur and tibia at all times. This visualization depicts all of the anatomical landmarks, surfaces, and axes registered with the pointer device during the surgery. The visualization also shows derived geometry such as the joint centers and the mechanical axis of the knee. Furthermore, the visualization provides a running update of the flexion angle of the knee, the internal/external rotation of the femur and tibia, and the extent of any varus/valgus deformity. The surgeon can zoom in and out, rotate the viewing angle, and hide bones, text, or registered geometry. Finally, the visualization can make position and orientation measurements between registered points, surfaces, and axes. The benefit of the visualization is that it allows the surgeon to see the inner workings of the software algorithms and use common sense measures to ascertain that the calculated computer geometry is in fact accurate. The visualization is present in addition to the regular part of the user interface that guides the surgeon through the procedure and prompts him or her for data.

FIG. 20 also depicts all of the anatomical landmarks, surfaces, and axes used by the inertial based surgical navigation system. In the present embodiment of the invention, the anatomical landmarks, surfaces, and axes would include but not be limited to:

1) The medial and lateral malleolus
2) A medial, lateral, and anterior contour point along the tibia
3) The mechanical axis point of the tibia
4) The medial and lateral surfaces of the tibia
5) The anterior surface of the tibia
6) The anteroposterior axis of the tibia
7) The medial and lateral epicondyles of the femur
8) The anterior cortex point of the femur
9) The mechanical axis point of the femur
10) The most anterior, distal, and posterior points for the medial condyle of the femur
11) The most anterior, distal, and posterior points for the lateral condyle of the femur
12) The medial and lateral condyle surfaces of the femur
13) The anterior surface of the femur
14) The anteroposterior axis of the femur The computer system is coded in LabVIEW using a queued state machine architecture. In an alternate embodiment of the invention, a three-dimensional CAD software package known as Rhinoceros is used in conjunction with LabVIEW to render complex images. Alternate embodiments of the invention could be coded in a different programming language and use different three-dimensional rendering software.

The invention claimed is:

1. A surgical navigation system comprising:
a first inertial sensor that measures its own motion without an external reference and in response thereto provides data relating to a position and an orientation of said first inertial sensor, said first inertial sensor being configured to attach to a patient's body;
a sensor processor that receives said data from said first inertial sensor and using said data calculates the position of said first inertial sensor and the orientation of said first inertial sensor in a common coordinate system that defines position and orientation coordinates relative to an initial position and an initial orientation of the first inertial sensor;
a mapping processor that stores in memory an initial location of a point on the patient's body and determines a location of said point on the patient's body in the common coordinate system based on the position and orientation of said first inertial sensor after the patient's body has moved, wherein the mapping processor computes from the determined location of said point on the patient's body, a point display element that represents a graphical depiction of the location of said point on the patient's body in the common coordinate system; and
a display in communication with the mapping processor, the display comprising a graphical user interface that receives the point display element from the mapping processor and displays the point display element to provide a graphical depiction of the determined location of said point on the patient's body relative to a planned surgical cut, thereby providing feedback as to an alignment of the patient's body with the planned surgical cut.

2. The surgical navigation system as recited in claim 1, wherein said sensor processor processes said data with a Kalman filter.

3. The surgical navigation system as recited in claim 1, wherein said first inertial sensor comprises at least two inertial chips.

4. The surgical navigation system as recited in claim 1, wherein said first inertial sensor is configured to compensate for temperature fluctuations in said first inertial sensor.

5. The surgical navigation system as recited in claim 1, wherein the graphical user interface displays a graphical depiction of said patient's body together with the point display element to represent a location of said first inertial sensor on said patient's body.

6. The surgical navigation system as recited in claim 1, further comprising a pointer device comprising:
a housing that extends from a distal end to a proximal end;
a tip located at the proximal end of the housing; and
wherein the pointer device is configured to provide a position and an orientation of said pointer device to said mapping processor, said mapping processor being configured to calculate position and orientation coordinates of a location of said pointer device in the common coordinate system defined by the initial position and the initial orientation of said first inertial sensor.

7. The surgical navigation system as recited in claim 1, further comprising a second inertial sensor that measures its own motion without an external reference and in response thereto provides data relating to a position and an orientation of said second inertial sensor, said second inertial sensor being configured to attach to a surgical instrument.

8. The surgical navigation system as recited in claim 7, wherein:
said sensor processor receives said data from said second inertial sensor and calculates the position of said second inertial sensor and the orientation of said second inertial sensor in the common coordinate system;
said mapping processor is configured to determine a position and an orientation of said surgical instrument relative to a planned position and orientation of said surgical instrument based on the position and orientation of said first and second inertial sensors, wherein the position and orientation of said surgical instrument is determined in the common coordinate system and wherein the mapping processor computes from the determined position and orientation of said surgical instrument, a surgical instrument display element that represents a graphical depiction of the position and orientation of said surgical instrument; and
said display receives the surgical instrument display element from the mapping processor and displays the surgical instrument display element to provide a graphical depiction of the surgical instrument relative to the planned surgical cut, thereby providing feedback as to an alignment of the surgical instrument with the planned surgical cut.

9. The surgical navigation system as recited in claim 8, wherein the graphical user interface displays a graphical depiction of said patient's body together with the surgical instrument display element to represent the position and orientation of the surgical instrument relative to said patient's body.

10. The surgical navigation system as recited in claim 1, wherein said mapping processor determines a center of a hip joint by tracking the location of said point on the patient's body when the patient's body is moved and to calculate a common radius to the tracked locations of said point while the patient's body was moved.

11. The surgical navigation system as recited in claim 1 further comprising a memory that is accessible by said mapping processor, said memory having stored thereon a geometry database containing geometrical information regarding human anatomy.

12. The surgical navigation system as recited in claim 1 further comprising a housing, wherein said first inertial sensor and said sensor processor are contained in the housing.

13. The surgical navigation system as recited in claim 1, further comprising an inertial sensor hub that communicates with said first inertial sensor and stores tracked locations of said first inertial sensor.

14. The surgical navigation system as recited in claim 1 further comprising a calibration device for calibrating said first inertial sensor and other inertial sensors relative to the common coordinate system prior to using said first inertial sensor, wherein the calibration device is configured to hold the first inertial sensor and the other inertial sensors at known positions and orientations relative to one another, such that the common coordinate system can be defined relative to the initial position and the initial orientation of the first inertial sensor so that positions and orientations of the first inertial sensor and the other inertial sensors are defined by the position and orientation coordinates in the common coordinate system.

15. The surgical navigation system as recited in claim 6, wherein said pointer device has coupled thereto an inertial sensor that measures its own motion without an external reference and in response thereto provides data relating to the position and the orientation of said pointer device to said mapping processor.

16. The surgical navigation system as recited in claim 2, wherein said first inertial sensor comprises at least two inertial chips that each measure the motion of the first inertial sensor by sensing their own motion in six degrees-of-freedom, and wherein the Kalman filter operates on redundant measurements obtained from the at least two inertial chips.

17. The surgical navigation system as recited in claim 16, wherein the at least two inertial chips comprise at least a first inertial chip having sensitive axes along which the first inertial chip senses its own motion in six degrees-of-freedom and a second inertial chip having sensitive axes along which the second inertial chip senses its own motion in six degrees-of-freedom, wherein the first inertial chip and the second inertial chip are arranged in the first inertial sensor such that the sensitive axes of the first inertial chip are parallel to respective ones of sensitive axes of the second inertial chip such that redundant measurements are obtained from the at least two inertial chips.

18. The surgical navigation system as recited in claim 8, wherein the surgical instrument is a cut guide and the planned surgical cut indicates a planned cutting plane.

19. The surgical navigation system as recited in claim 18, wherein the mapping processor tracks the position and orientation of the cut guide relative to the planned position and orientation of the cut guide and computes a cut guide display element that represents a graphical depiction of the tracked position and orientation of the cut guide so as to allow alignment of a cutting plane of the cut guide with a planned cutting plane.

20. The surgical navigation system as recited in claim 19, wherein the graphical user interface receives and displays body display element that represents a graphical depiction of said patient's body and at least one of:
  the cut guide display element to represent the position and orientation of the cut guide relative to said patient's body;
  a cutting plane display element that represents a graphical depiction of the position and orientation of the cutting plane relative to said patient's body; and
  a planned cutting plane display element that represents a graphical depiction of the position and orientation of the planned cutting plane relative to said patient's body.

21. The surgical navigation system as recited in claim 11, wherein the geometry database stored on the memory also contains computer-aided design (CAD) data for a plurality of different surgical tools and implants.

22. A surgical navigation system, comprising:
  at least one inertial sensor that measures its own motion without an external reference and is configured to be removably attached to an object, wherein the object is at least one of a portion of a patient's anatomy and a surgical instrument;
  a sensor processor in communication with the at least one inertial sensor to receive from the at least one inertial sensor, data indicative of a position and an orientation of the at least one inertial sensor in a common coordinate system that defines position and orientation coordinates relative to an initial position and an initial orientation of the at least one inertial sensor; and
  a computer system in communication with the sensor processor to receive the data from the sensor processor; compute, from the received data, a position and an orientation of the object in the common coordinate system; and provide feedback to a user that indicates an alignment of the object to a planned surgical cut based on the computed position and orientation of the object.

23. The surgical navigation system as recited in claim 22, further comprising a display in communication with the computer system, and wherein the computer system computes an object display element from the computed position and orientation of the object in the common coordinate system and the display comprises a graphical user interface that receives the object display element from the computer system and displays the object display element to provide a graphical depiction of the position and orientation of the object and displays a planned surgical cut display element that provides a graphical depiction of a position and an orientation of the planned surgical cut, thereby providing the feedback to the user.

24. The surgical navigation system as recited in claim 23, wherein the planned surgical cut indicates a planned resection plane, and wherein the graphical user interface displays planned surgical cut display element and the object display element together to provide a graphical depiction of the position and orientation of the planned resection plane relative to the position and orientation of the object in the common coordinate system.

25. The surgical navigation system as recited in claim 23, wherein the computer system determines information associated with an alignment of the position and orientation of the planned surgical cut with the position and orientation of the object, and the display receives and displays the information associated with the alignment of the position and orientation of the planned surgical cut together with the object display element.

26. The surgical navigation system as recited in claim 23, wherein the object is a surgical instrument and the display displays the object display element together with the planned surgical cut display element to provide a graphical depiction of the position and orientation of the surgical instrument relative to the position and orientation of the planned surgical cut in the common coordinate system.

27. The surgical navigation system as recited in claim 26, wherein the display receives and displays a patient anatomy display element together with the object display element and the planned surgical cut display element to provide a graphical depiction of a position and orientation of a portion of the patient's anatomy relative to the position and orientation of the planned surgical cut and the position and orientation of the surgical instrument in the common coordinate system.

28. The surgical navigation system as recited in claim 27, further comprising a second inertial sensor that measures its own motion without an external reference and is configured to be removably attached to the portion of the patient's anatomy, and wherein the position and orientation of the portion of the patient's anatomy is determined from data received from the second inertial sensor and the position and orientation of the portion of the patient's anatomy is determined in the common coordinate system.

29. The surgical navigation system as recited in claim 23, wherein the object is a surgical implant and the graphical user interface displays the object display element together with a planned position display element that provides a graphical depiction of a planned position and orientation of the surgical implant, thereby providing the user feedback related to the position and orientation of the surgical implant relative to the planned position and orientation of the surgical implant in the common coordinate system.

30. The surgical navigation system as recited in claim 22, further comprising a pointer device comprising:
  a housing that extends from a distal end to a proximal end;
  a tip located at the proximal end of the housing; and
  wherein the pointer device is in communication with the sensor processor to record a position and orientation of the tip of the pointer device as a reference point in the common coordinate system.

31. The surgical navigation system as recited in claim 30, wherein the reference point is an anatomical landmark recorded as a position and orientation of a point on a portion of the patient's anatomy.

32. The surgical navigation system as recited in claim 30, wherein the pointer device further comprises at least one inertial sensor coupled to the pointer device and that measures its own motion without an external reference and in response thereto provides data relating to the position and orientation of the tip of the pointer device in the common coordinate system.

33. The surgical navigation system as recited in claim 30, further comprising a display in communication with the computer system, and wherein the computer system computes a reference point display element from the recorded reference point and an object display element from the computed position and orientation of the object in the common coordinate system, and wherein the display comprises a graphical user interface that receives and displays the reference point display element and the object display element to provide a graphical depiction of the position and orientation of the reference point relative to the position and orientation of the object in the common coordinate system.

34. The surgical navigation system as recited in claim 33, wherein the at least one reference point is associated with a point on a portion of the patient's anatomy and the graphical user interface displays movement of the portion of the patient's anatomy as movement of the at least one reference point relative to the position and orientation of the object.

35. The surgical navigation system as recited in claim 34, wherein the portion of the patient's anatomy is a bone and the computer system computes a joint center from the position and orientation of the at least one reference point as the bone is moved.

36. The surgical navigation system as recited in claim 22, wherein the object is a portion of the patient's anatomy and the computer system computes data associated with a difference between the position and orientation of the portion of the patient's anatomy and a position and orientation of another point in the common coordinate system.

37. The surgical navigation system as recited in claim 36, wherein the position and orientation of the another point is provided in the common coordinate system by another inertial sensor in communication with the sensor processor.

38. The surgical navigation system as recited in claim 37, wherein the other inertial sensor measures its own motion without an external reference and is configured to be removably attached to a second object, wherein the second object is at least one of another portion of the patient's anatomy and a surgical instrument.

39. A surgical navigation system, comprising:
a plurality of inertial sensors comprising at least one inertial sensor configured to be removably attached to a bone and at least one inertial sensor configured to be removably attached to a surgical instrument, wherein each of the plurality of inertial sensors measures its own motion without an external reference and in response thereto provides data relating to a position and an orientation of said inertial sensor;
a sensor processor in communication with the plurality of inertial sensors and configured to receive from the plurality of inertial sensors, data indicative of positions and orientations of the plurality of inertial sensors in a common coordinate system that defines position and orientation coordinates relative to an initial position and an initial orientation of one of the plurality of inertial sensors;
a computer system in communication with the sensor processor and configured to:
receive the data from the sensor processor;
compute from the received data, a position and an orientation of the bone in the common coordinate system;
compute from the received data, a position and an orientation of the surgical instrument in the common coordinate system;
compute from the position and orientation of the bone, a bone display element that represents a graphical depiction of the position and orientation of the bone in the common coordinate system;
compute from the position and orientation of the surgical instrument, a surgical instrument display element that represents a graphical depiction of the position and orientation of the surgical instrument in the common coordinate system; and
a display in communication with the computer system, the display comprising a graphical user interface that receives the bone display element and the surgical instrument display element from the computer system and displays the bone display element together with the surgical instrument display element to provide a graphical depiction of both the computed position and orientation of the bone and the computed position and orientation of the surgical instrument relative to each other in the common coordinate system, thereby providing feedback to a user as to an alignment of the surgical instrument with a location on the bone.

40. The surgical navigation system as recited in claim 39, wherein the surgical instrument is a cut guide.

41. The surgical navigation system as recited in claim 39, wherein the surgical instrument is a surgical implant.

42. The surgical navigation system as recited in claim 41, wherein the surgical implant is a prosthesis.

43. The surgical navigation system as recited in claim 42, wherein the computer system is configured to determine an optimal position and orientation of the prosthesis based on the computed position and orientation of the bone.

44. The surgical navigation system as recited in claim 39, wherein the computer system determines a planned cutting plane based on the computed position and orientation of the bone and computes a planned cutting plane display element from the determined cutting plane, and the graphical user interface also receives and displays the planned cutting plane display element to provide a graphical depiction of the planned cutting plane relative to the positions and orientations of the bone and the surgical instrument in the common coordinate system.

45. The surgical navigation system as recited in claim 39, wherein the computer system determines a joint center by tracking the computed position and orientation of the bone as the bone moves through a plurality of different positions and orientations.

46. The surgical navigation system as recited in claim 1, wherein the first inertial sensor further comprises a magnetometer that generates angular velocity data by measuring its orientation with respect to a magnetic axis of Earth, and wherein the sensor processor receives and uses the angular velocity data when calculating the position and orientation of said first inertial sensor in the common coordinate system.

* * * * *